United States Patent
Müller et al.

[11] Patent Number: 5,919,807
[45] Date of Patent: Jul. 6, 1999

[54] BENZOTHIAZOLES AND BENZOXAZOLES, DRUGS CONTAINING THEM, THEIR USE AND METHODS OF PREPARING THEM

[75] Inventors: Peter Müller, Stamford, Conn.; Rudolph Hurnaus, Biberach, Germany; Roland Maier, Biberach, Germany; Michael Mark, Biberach, Germany; Bernhard Eisele, Biberach, Germany; Ralph-Michael Budzinski, Biberach, Germany; Leo Thomas, Biberach, Germany; Gerhard Hallermayer, Maselheim, Germany

[73] Assignee: Dr. Karl Thomae GmbH, Biberach, Germany

[21] Appl. No.: 08/945,612

[22] PCT Filed: May 2, 1996

[86] PCT No.: PCT/EP96/01827

§ 371 Date: Oct. 28, 1997

§ 102(e) Date: Oct. 28, 1997

[87] PCT Pub. No.: WO96/35681

PCT Pub. Date: Nov. 14, 1996

[30] Foreign Application Priority Data

May 12, 1995 [DE] Germany ............... 195 17 448

[51] Int. Cl.[6] ............ A61K 31/425; C07D 277/74; C07D 277/82; C07D 277/68
[52] U.S. Cl. .............. 514/367; 548/161; 548/169
[58] Field of Search ............ 514/367; 548/161, 548/169

[56] References Cited

U.S. PATENT DOCUMENTS 2,578,757  3/1949  Steiger et al. .............. 260/293.4

FOREIGN PATENT DOCUMENTS

A 0030632  6/1981  European Pat. Off. .

OTHER PUBLICATIONS

The Merck Index, 1989, Merck & Company, Rahway, N.J. (see Diamthazole Dihydrochloride(compound No. 2967, on p. 2974).

Chemical Abstracts Registry Handbook–Number Section, 1991 Supplement, Registry Nos. 132979–00–1–thru 134653–09–1, see compound with RN=133688–59–2.

Chemical Abstracts, vol. 114, No. 21, 1991, Abstract No. 207259j, Nishi, T., et al: "Preparation of Benzothiazoles and benzimidazoles as Blood Platelet Aggregation Inhibitors".

Chemical Abstracts, vol. 54, No. 11. Jun. 10, 1980; Abstract No. 11052d, Crookes Laboratories Ltd. (by F. Stephens), Brit. 825 016, "Therapeutic Derivatives of Arylbenzothiazoles", see 6–diethylaminoethoxy–2–(p–chlorophenyl) benzothiazole.

Chemical Abstracts Registry Handbook–Number Section, 1972, "Registry Nos. 33913–69–8 thru 38053–994–0" see RN=36612–16–5.

*Primary Examiner*—Laura L. Stockton
*Attorney, Agent, or Firm*—Robert P. Raymond; Alan R. Stempel; Mary-Ellen Devlin

[57] ABSTRACT

The invention relates to benzothiazoles and benzoxazoles of general formula

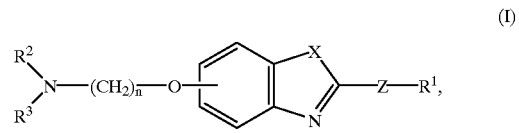

(I)

wherein $R^1$ to $R^3$, X, Z and n are defined as in claim 1, the enantiomers, diastereomers and salts thereof, particularly the physiologically acceptable acid addition salts thereof which have valuable properties, particularly an inhibitory effect on cholesterol biosynthesis, pharmaceutical compositions containing these compounds, the use thereof and processes for preparing them.

14 Claims, No Drawings

BENZOTHIAZOLES AND BENZOXAZOLES, DRUGS CONTAINING THEM, THEIR USE AND METHODS OF PREPARING THEM

This application is a 371 of PCT/EP96/01827 filed May 2, 1996.

The present invention relates to new benzothiazoles and benzoxazoles, the salts thereof with physiologically acceptable organic and inorganic acids, processes for preparing these compounds and pharmaceutical compositions containing them.

The compounds according to the invention are inhibitors of cholesterol biosynthesis, and more particularly inhibitors of the enzyme 2,3-epoxysqualene-lanosterol-cyclase, a key enzyme of cholesterol biosynthesis. The compounds according to the invention are suitable for the treatment and prevention of hyperlipidaemia, hypercholesterolaemia and atherosclerosis. Other possible uses include the treatment of hyperproliferative skin and vascular diseases, tumours, gallstones and mycoses.

Compounds which intervene in cholesterol biosynthesis are important for the treatment of a number of syndromes. Particular mention should be made of hypercholesterolaemias and hyperlipidaemias which are risk factors for the formation of atherosclerotic vascular changes and diseases resulting therefrom such as coronary heart disease, cerebral ischaemia, Claudicatio intermittens and gangrene.

The significance of excessively high serum-cholesterol levels as the chief risk factor for the occurrence of atherosclerotic vascular changes is generally recognised.

Extensive clinical trials have shown that by reducing the serum cholesterol the risk of suffering from coronary heart diseases can be reduced (Current Opinion in Lipidology 2(4), 234 [1991]). Since the majority of the cholesterol is synthesised in the body itself and only a small part is taken with the food, inhibiting biosynthesis is a particularly attractive way of lowering the raised cholesterol level.

In addition, other possible uses for cholesterol biosynthesis inhibitors are the treatment of hyperproliferative skin and vascular disorders and tumour diseases, the treatment and prevention of gallstone problems and use in mycoses. The latter is concerned with intervention in ergosterol biosynthesis in fungal organisms which largely progresses analogously to cholesterol biosynthesis in mammalian cells.

Cholesterol or ergosterol biosynthesis proceeds, starting from acetic acid, through a fairly large number of reaction steps. This multi-step process offers a number of ways of intervening, of which the following are given by way of example:

For inhibiting the enzyme 3-hydroxy-3-methylglutaryl-coenzyme A (HMG-CoA)-synthase, β-lactones and β-lactams with a potential antihypercholesterolaemic activity are mentioned (see J. Antibiotics 40, 1356 [1987], U.S. Pat. No. 4,751,237, EP-A-0 462 667, U.S. Pat. No. 4,983, 597).

Inhibitors of the enzyme HMG-CoA-reductase are 3,5-dihydroxycarboxylic acids of the Mevinolin type and the δ-lactones thereof; Lovastatin, Simvastatin and Pravastatin are examples of these which are used in the treatment of hypercholesterolaemias. Other applications for these compounds are fungal infections (U.S. Pat. No. 4,375,475, EP-A-0 113 881, U.S. Pat. No. 5,106,992), skin diseases (EP-A-0 369 263) and gallstone problems and tumour diseases (U.S. Pat. No. 5,106,992; Lancet 339, 1154–1156 [1992]). Inhibiting the proliferation of smooth muscle cells by means of Lovastatin is described in Cardiovasc. Drugs. Ther. 5, Suppl. 3, 354 [1991].

Inhibitors of the enzyme squalene-synthetase include, for example, isoprenoid-(phosphinylmethyl)phosphonates, the suitability of which for the treatment of hypercholesterolaemia, gallstone problems and tumour diseases is described in EP-A-0 409 181 and J. Med. Chemistry 34, 1912 [1991], and also the squalestatines with a cholesterol-lowering and antimycotic activity (J. Antibiotics 5, 639–647 [1992] and J. Biol. Chemistry 267, 11705–11708 [1992].

Known inhibitors of the enzyme squalene-epoxidase are the allylamines such as Naftifin and Terbinafin, which have been used in therapy as agents for treating fungal diseases, as well as allylamine NB-598 with an antihypercholesterolaemic activity (J. Biol. Chemistry 265, 18075–18078, [1990]) and fluorosqualene derivatives with a hypocholesterolaemic activity (U.S. Pat. No. 5,011,859). Piperidines and azadecalines with a potential hypocholesterolaemic and/ or antifungal activity are also described, although the mechanism of activity is not clearly established, these compounds being squalene epoxidase- and/or 2,3-epoxisqualene-lanosterol-cyclase inhibitors (EP-A-0 420 116, EP-A-0 468 434, U.S. Pat. No. 5,084,461 and EP-A-0 468 457).

Examples of inhibitors of the enzyme 2,3-epoxisqualene-lanosterol-cyclase are diphenyl derivatives (EP-A-0 464 465), aminoalkoxybenzene derivatives (EP-A-0 410 359), aminoalkyl derivatives (EP-A-0 401 798, U.S. Pat. No. 5,214,546, EP-A-0 636 367) and piperidine derivatives (J. Org. Chem. 57, 2794–2803, [1992]). Moreover, this enzyme is inhibited in mammalian cells by decalines, azadecalines and indane derivatives (WO 89/08450, J. Biol. Chemistry 254, 11258–11263 [1981], Biochem. Pharmacology 37, 1955–1964 [1988] and J 64 003 144), and also by 2-aza-2, 3-dihydrosqualene and 2,3-epiminosqualene (Biochem. Pharmacology 34, 2765–2777 [1985]), by squalenoid-epoxide-vinylether (J. Chem. Soc. Perkin Trans. I, 1988, 461) and 29-methylidene-2,3-oxidosqualene (J. Amer. Chem. Soc. 113, 9673–9674 [1991]).

Finally, inhibitors of the enzyme lanosterol-14α-demethylase are steroid derivatives with a potential antihyperlipaemic activity, which simultaneously influence the enzyme HMG-CoA-reductase (U.S. Pat. No. 5,041,432, J. Biol. Chemistry 266, 20070–20078 [1991], U.S. Pat. No. 5,034,548). Moreover, this enzyme is inhibited by antimycotics of the azole type which constitute N-substituted imidazoles and triazoles. This category includes, for example, the commercially available antimycotics ketoconazole and fluconazole.

The compounds of general formula I which follows are new. It has surprisingly been found that they are highly effective inhibitors of the enzyme 2,3-epoxisqualene-lanosterol-cyclase (International Classification: EC5.4.99.7).

The enzyme 2,3-epoxisqualene-lanosterol-cyclase catalyses a key step in cholesterol and ergosterol biosynthesis, namely the conversion of 2,3-epoxisqualene into lanosterol, the first compound having a steroid structure in the biosynthesis cascade. Inhibitors of this enzyme lead one to expect the advantage of higher selectivity compared with inhibitors of earlier biosynthesis steps, such as HMG-CoA-synthase and HMG-CoA-reductase, since inhibition of these early biosynthesis steps leads to a reduction in biosynthetically formed mevalonic acid and consequently may have a negative effect on the biosynthesis of the mevalonic acid-dependent substances dolichol, ubiquinone and isopentenyl-t-RNA (cf. J. Biol. Chemistry 265, 18075–18078 [1990]).

During inhibition of biosynthesis steps after the conversion of 2,3-epoxysqualene into lanosterol there is the risk of the accumulation of intermediate products with a steroid structure in the body and the triggering of toxic effects caused by them. This has been described, for example, in the case of triparanol, a desmosterol reductase inhibitor. This substance had to be taken off the market owing to the formation of cataracts, ichthyosis and alopecia (mentioned in J. Biol. Chemistry 265, 18075–18078 [1990]).

As already explained hereinbefore, inhibitors of 2,3-epoxysqualene-lanosterol-cyclase are individually described in the literature. However, the structures of these compounds are completely different from the structure of the compounds of general formula I below according to the invention.

The invention relates to the preparation of antihypercholesterolaemic substances which are suitable for the treatment and prevention of atherosclerosis and, compared with known active substances, are characterised by a better antihypercholesterolaemic activity with increased selectivity and hence increased safety. Since the compounds according to the invention are also able to inhibit ergosterol biosynthesis in the fungal organism on account of their great efficacy as inhibitors of the enzyme 2,3-epoxysqualene-lanosterol-cyclase, they are also suitable for the treatment of mycoses.

The present invention relates to the new benzothiazoles and benzoxazoles of general formula

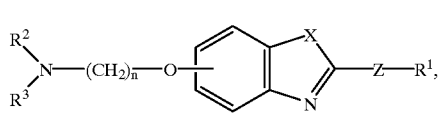

(I)

wherein n denotes the number 2, 3, 4, 5 or 6,

X is an oxygen or sulphur atom,

Z is a bond, an oxygen or sulphur atom, an imino group in which the hydrogen atom may be replaced by a $C_{1-3}$-alkyl group, or a sulphonyl group, $R^1$ denotes a triphenylmethyl, phenyl or pyridyl group, a straight-chained or branched $C_{1-8}$-alkyl group or a straight-chained $C_{2-6}$-alkenyl group, which may optionally be substituted by 1 to 3 methyl groups, whilst both the alkyl group and the alkenyl group may be terminally substituted by a $C_{3-7}$-cycloalkyl group, by a phenyl or naphthyl group, by a 5-membered heteroaryl group bound via a carbon atom which contains an optionally alkyl-substituted imino group, an oxygen or sulphur atom or a nitrogen atom and an oxygen or sulphur atom or an optionally alkyl-substituted imino group, or by a 6-membered heteroaryl group bound via a carbon atom and containing 1 or 2 nitrogen atoms, whilst the above-mentioned phenyl groups may each be mono- or disubstituted by a halogen atom, an alkyl, trifluoromethyl, cyano or nitro group, $R^2$ and $R^3$, which may be identical or different, each denote a straight-chained or branched $C_{1-6}$-alkyl group which may be terminally substituted by a hydroxy, alkyloxy or alkylcarbonyloxy group, wherein the alkyl moieties may in each case be straight-chained or branched and may comprise 1 to 6 carbon atoms, or a straight-chained or branched $C_{3-6}$-alkenyl group, or $R^2$ and $R^3$ together with the nitrogen atom between them denote a 5-, 6- or 7-membered saturated monocyclic ring, whilst in a 6- or 7-membered ring thus formed a methylene group in the 4-position may be replaced by an oxygen atom or an —NH— group and the hydrogen atom in the —NH— group may be replaced by an alkyl group and the above-mentioned 5-, 6- or 7-membered rings may additionally be substituted in the carbon skeleton by one or two alkyl groups, whilst a halogen atom as mentioned hereinbefore denotes a fluorine, chlorine, bromine or iodine atom and unless otherwise specified an alkyl group may contain 1 to 3 carbon atoms, the enantiomers, diastereomers and the salts thereof, particularly the physiologically acceptable acid addition salts thereof.

Examples of 5- or 6-membered heteroaryl groups as mentioned in the above definition include the 2-thienyl, 3-thienyl, 2-furyl, 3-furyl, 1H-pyrrol-2-yl, 1H-pyrrol-3-yl, 1-methylpyrrol-2-yl, 1-methylpyrrol-3-yl, 2-imidazolyl, 4-imidazolyl, 1,3-oxazol-2-yl, 1,3-oxazol-4-yl, 1,3-oxazol-5-yl, 3-pyrazolyl, 4-pyrazolyl, 3-isoxazolyl, 4-isoxazolyl, 5-isoxazolyl, 2-pyridyl, 3-pyridyl, 4-pyridyl, pyrazinyl, 2-pyrimidinyl, 4-pyrimidinyl, 5-pyrimidinyl, 3-pyridazinyl, or 4-pyridazinyl group.

Preferred compounds are the benzothiazoles of the above general formula I, particularly the benzothiazoles of general formula Ia

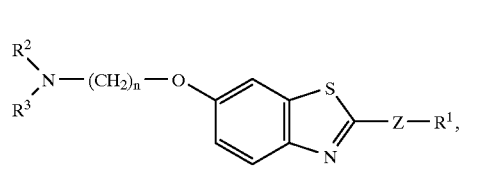

(Ia)

wherein n, Z and $R^1$ to $R^3$ are as hereinbefore defined, the enantiomers, diastereomers and salts thereof.

Most particularly preferred are the benzothiazoles of the above general formula Ia, wherein n denotes the number 2, 3, 4, 5 or 6, Z denotes a bond, an N-methyl-imino group, an oxygen or sulphur atom, $R^1$ denotes a phenyl, 2- or 4-pyridyl group, a straight-chained $C_{1-5}$-alkyl group optionally substituted by 1 to 3 methyl groups, whilst a straight-chained $C_{1-3}$-alkyl group may additionally be terminally substituted by a $C_{5\ or\ 6}$-cycloalkyl ring, by a phenyl, 1-naphthyl, 2-naphthyl, 2-thienyl, 1H-pyrrol-2-yl, 1H-pyrrol-3-yl, 1-methylpyrrol-2-yl, 1-methylpyrrol-3-yl, 2-pyridyl or 4-pyridyl group, or a 2-phenylethenyl group, whilst the above-mentioned phenyl groups may each be mono-substituted by a fluorine or chlorine atom or by a methyl, trifluoromethyl, cyano or nitro group or may be disubstituted by a methyl and a nitro group, $R^2$ and $R^3$, which may be identical or different, each denote a straight-chained or branched $C_{1-3}$-alkyl group which may be terminally substituted by a hydroxy, alkyloxy or alkylcarbonyloxy group, whilst the alkyl moieties in each case may be straight-chained or branched and may contain 1 to 4 carbon atoms, or an allyl group, or $R^2$ and $R^3$ together with the nitrogen atom between them denote a 1-pyrrolidinyl, 1-piperidinyl, 2,6-dimethyl-1-piperidinyl, 1-piperazinyl, 4-methyl-1-piperazinyl or 4-morpholinyl ring, the enantiomers, diastereomers and salts thereof, in particular the benzothiazoles of general formula Ia
wherein
n denotes the number 2,
Z is a bond and
R¹ is a methyl group which is substituted by a phenyl group optionally substituted in the 4-position by a fluorine or chlorine atom or a methyl or trifluoromethyl group, or is substituted by a 1-methylpyrrol-3-yl group, or
Z denotes a sulphur atom and
R¹ denotes a 2,2-dimethyl-propyl, 4-chlorophenyl, 4-fluorophenyl, 4-chlorobenzyl or 4-fluorobenzyl group,
R² and R³, which may be identical or different, denotes a methyl, ethyl or 2-hydroxyethyl group, and the salts thereof.

The following are mentioned as examples of particularly preferred compounds:

(1) 6-(2-Dimethylamino-ethoxy)-2-(4-fluorobenzyl)-benzothiazole,
(2) 6-(2-Diethylamino-ethoxy)-2-(4-fluorobenzyl)-benzothiazole,
(3) 6-[2-(N-(2-Hydroxyethyl)-N-methyl-amino)ethoxy]-2-[4-(trifluoromethyl)benzyl]-benzothiazole,
(4) 6-(2-Diethylamino-ethoxy)-2-(1-methylpyrrolyl-3-methyl)-benzothiazole,
(5) 6-[2-(N.N-Bis-(2-hydroxyethyl)amino)ethoxy]-2-(4-fluorobenzyl)-benzothiazole,
(6) 6-[2-(N.N-Bis-(2-hydroxyethyl)amino)ethoxy]-2-(4-chlorophenylmercapto)-benzothiazole,
(7) 2-(4-Chlorobenzyl)-6-[2-(N-ethyl-N-(2-hydroxyethyl)amino)-ethoxy]-benzothiazole,
(8) 6-[N.N-Bis-(2-hydroxyethyl)amino)ethoxy]-2-(4-chlorobenzyl)-benzothiazole,
(9) 6-[2-(N.N-Bis-(2-hydroxyethyl)amino)ethoxy]-2-[4-(trifluoromethyl)benzyl]-benzothiazole,
(10) 2-(4-Chlorobenzyl)-6-[2-(N-(2-hydroxyethyl)-N-methyl-amino)ethoxy]-benzothiazole,
(11) 2-(4-Chlorobenzyl)-6-(2-diethylamino-ethoxy)-benzothiazole,
(12) 2-(4-Chlorobenzylmercapto)-6-(2-diethylamino-ethoxy)-benzothiazole,
(13) 6-(2-Diethylamino-ethoxy)-2-(2,2-dimethyl-propylmercapto)-benzothiazole,
(14) 2-(4-Chlorophenylmercapto)-6-(2-diethylamino-ethoxy)-benzothiazole,
(15) 6-(2-Diethylamino-ethoxy)-2-(4-fluorophenylmercapto)-benzothiazole,
(16) 2-(4-Fluorophenylmercapto)-6-[2-(N-(2-hydroxyethyl)-N-methyl-amino)ethoxy]-benzothiazole,
(17) 2-(4-Chlorophenylmercapto)-6-[2-(N-ethyl-N-(2-hydroxyethyl)amino)ethoxy]-benzothiazole
and the salts thereof.

The compounds of general formula I may be prepared, for example, using the following methods:
a) Reacting a compound of general formula (II)

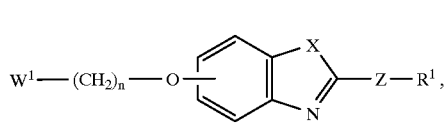

wherein
n, X, Z and R¹ are as hereinbefore defined and W¹ denotes a reactive leaving group, e.g. a chlorine, bromine or iodine atom or a sulphonic acid ester grouping, e.g. a methanesulphonyloxy or toluenesulphonyloxy group, with an amine of general formula (III)

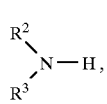

wherein
R² and R³ are as hereinbefore defined.

The reaction is conveniently carried out in a suitable solvent such as ethanol, ethyl acetate, methylene chloride, acetonitrile or dimethylformamide, optionally in the presence of a base such as sodium carbonate, potassium carbonate or triethylamine, or in an excess of a compound of formula III, optionally in the presence of a reaction accelerator such as potassium or sodium iodide, at a temperature between 0° C. and 120° C., but preferably at a temperature between 50° C. and 120° C.

b) In order to prepare compounds of general formula I, wherein at least one of the groups R² and R³ denotes a straight-chained or branched $C_{1-6}$-alkyl group terminally substituted by an alkylcarbonyloxy group:
Acylating a compound of general formula (IV)

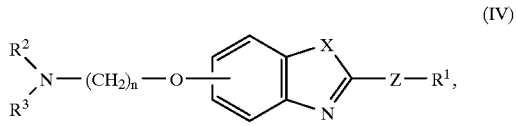

wherein
n, X, Z and R¹ to R³ are as hereinbefore defined, with the proviso that at least one of the groups R² or R³ denotes a straight-chained or branched $C_{1-6}$-alkyl group terminally substituted by a hydroxy group,
with an activated acid derivative of general formula (V)

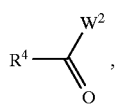

wherein
R⁴ denotes a straight-chained or branched $C_{1-6}$-alkyl group and
W² denotes a reactive leaving group, such as a chlorine, bromine or iodine atom or an imidazolide group.

The acylation is carried out in a suitable solvent such as ethyl acetate, tetrahydrofuran or methylene chloride in the presence of a base such as triethylamine or diisopropylethylamine.

c) Reacting a phenol of general formula (VI)

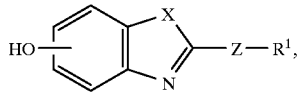

wherein
X, Z and R¹ are as hereinbefore defined, with an amine of general formula

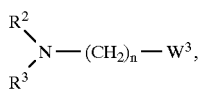
(VII)

wherein n, $R^2$ and $R^3$ are as hereinbefore defined and $W^3$ denotes a reactive leaving group, e.g. a chlorine, bromine or iodine atom or a sulphonic acid ester grouping such as the methanesulphonyloxy group, for example.

The reaction is conveniently carried out in a solvent such as acetonitrile, acetone, dimethylformamide or dimethylsulphoxide, optionally in the presence of a base such as sodium carbonate, potassium carbonate, sodium hydroxide, potassium hydroxide or sodium hydride, optionally in the presence of a reaction accelerator such as potassium or sodium iodide, at a temperature between 20° C. and 140° C., but preferably at a temperature between 50° C. and 140° C.

If the groups $R^2$ and/or $R^3$ in a compound of general formula VII contain free hydroxy groups, it is advisable to protect them in a suitable way before the reaction, e.g. by silylation with trialkylsilylchlorides and to cleave the protecting groups again using known methods after the reaction has ended.

d) In order to prepare compounds of general formula I wherein X is a sulphur atom and Z is an oxygen or sulphur atom, an —NH— group in which the hydrogen atom may be replaced by a $C_{1-3}$-alkyl group, or a sulphonyl group:

Reacting a compound of general formula

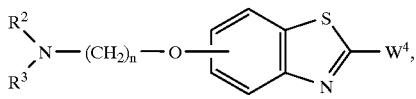
(VIII)

wherein n, $R^2$ and $R^3$ are as hereinbefore defined and $W^4$ denotes a reactive leaving group such as a chlorine or bromine atom, for example, with a compound of general formula

 (IX)

wherein $R^1$ and Z are as hereinbefore defined, with the exception of a bond.

The reaction is conveniently carried out in a suitable solvent such as, for example, tetrahydrofuran, acetonitrile or dimethylformamide, in the presence of a base such as sodium or potassium carbonate, potassium-tert.butoxide or sodium hydride. It is advisable, if the groups $R^2$ and/or $R^3$ in a compound of general formula VIII contain free hydroxy groups, to protect them in a suitable manner, e.g. by silylation, before the reaction and to cleave them again in known manner after the reaction has ended.

e) Reacting a compound of general formula

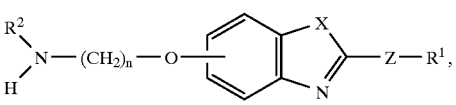
(X)

wherein $R^1$, $R^2$, X, Z and n are as hereinbefore defined, with a compound of general formula

 (XI)

wherein $R^3$ is as hereinbefore defined and $W^5$ denotes a reactive leaving group, e.g. a chlorine, bromine or iodine atom or a sulphonic acid ester grouping such as the methanesulphonyloxy group, for example.

The reaction is conveniently carried out in a solvent such as acetonitrile, acetone, dimethylformamide or dimethylsulphoxide, optionally in the presence of a base such as sodium carbonate, potassium carbonate, sodium hydroxide, potassium hydroxide or sodium hydride, optionally in the presence of a reaction accelerator such as potassium or sodium iodide, at a temperature between 20° C. and 140° C., but preferably at a temperature between 50° C. and 140° C.

If the groups $R^2$ and/or $R^3$ in a compound of general formula X and/or XI contain free hydroxy groups, it is advisable to protect them in a suitable manner before the reaction, e.g. by silylation with trialkylsilylchlorides and to cleave the protecting groups again using known methods after the reaction has ended.

The starting materials of general formula II can be obtained from the corresponding hydroxy compounds VI by alkylation with a 1,ω-dihaloalkane or with a 1,ω-haloalkanol according to Mitsunobu in the presence of triphenylphosphine and a dialkylazodicarboxylate, or with an alkylene carbonate such as ethylene or propylene carbonate and subsequently converting an ω-hydroxyalkoxy derivative thus obtained into a chloroalkoxy, bromoalkoxy, alkyl or arylsulphonyloxy derivative.

The alkylations with a 1,ω-dihaloalkane or an alkylene carbonate are conveniently carried out in a solvent such as acetonitrile or dimethylformamide in the presence of a base such as sodium or potassium carbonate at temperatures between 20° C. and 150° C., but preferably between 20° C. and 80° C. The reaction according to Mitsunobu is preferably carried out in glycoldimethylether or tetrahydrofuran at 0–20° C. The subsequent conversion of an ω-hydroxyalkoxy derivative into an ω-activated alkoxy derivative is carried out by alkylating the hydroxy group using methanesulphonic acid chloride or p-toluenesulphonic acid chloride or by halogenation according to Mitsunobu using carbon tetrachloride or carbon tetrabromide in the presence of triphenylphosphine.

The compounds of general formula VI are obtained from the corresponding methoxy or ethoxy compounds, which are known from the literature, or prepared by methods known from the literature [J. Chem. Soc. 1487 (1956), J. Org. Chem. 33, 2858 (1968)], by ether splitting using boron tribromide, pyridine hydrochloride or aluminium chloride.

The compounds of general formula VIII are obtained by diazotising a compound of general formula VIII wherein $W^4$ denotes an amino group or by alkylating a compound

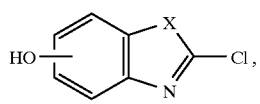 (XII)

with a compound of general formula VII.

A starting compound of general formula VIII or XII thus obtained can be converted, by reacting with a compound of general formula IX, into a corresponding compound wherein Z does not denote a bond. If, in a compound thus obtained, Z denotes a sulphur atom, this may be converted by oxidation into a corresponding compound wherein Z denotes a sulphinyl or sulphonyl group.

The compounds of general formula I have interesting biological properties. They are inhibitors of cholesterol biosynthesis, particularly inhibitors of the enzyme 2,3-epoxysqualene-lanosterol-cyclase. In view of their biological properties they are particularly suitable for the treatment and prevention of hypercholesterolaemia, hyperlipoproteinaemia and hypertriglyceridaemia and the resulting atherosclerotic vascular changes with the diseases resulting from them, such as coronary heart disease, cerebral ischaemia, Claudicatio intermittens, gangrene and others.

For treating these diseases, the compounds of general formula I may either be used on their own for monotherapy or may be used in conjunction with other cholesterol- or lipid-reducing substances, the compounds preferably being taken orally, but possibly in the form of suppositories by rectal route. Examples of possible combination partners include:

bile acid-binding resins such as cholestyramine, cholestipol and others, compounds which inhibit cholesterol resorption such as sitosterol and neomycin, compounds which affect cholesterol biosynthesis, such as HMG-CoA-reductase inhibitors such as lovastatin, simvastatin, pravastatin and others, squalene-epoxidase inhibitors such as NB 598 and analogous compounds and squalene synthetase inhibitors such as compounds of the category of the isoprenoid-(phosphinylmethyl) phosphonates and squalestatin.

Other possible combination partners which may be mentioned are the fibrates, such as clofibrate, bezafibrate, gemfibrozil and others, nicotinic acid, the derivatives and analogs thereof such as acipimox and probucol.

Moreover, the compounds of general formula I are suitable for treating diseases connected with excessive cell proliferation. Cholesterol is an essential component of cells and has to be present in sufficient quantities for cell proliferation, i.e. cell division. The inhibition of cell proliferation by inhibiting cholesterol biosynthesis has been described by means of the example of the smooth muscle cells with the HMG-CoA-reductase inhibitor of the mevinolin type lovastatin, as already mentioned hereinbefore.

Examples of diseases connected with excessive cell proliferation are primarily the tumour diseases. In cell culture and in vivo experiments it has been shown that the reduction of serum cholesterol or intervention in cholesterol biosynthesis by means of HMG-CoA-reductase inhibitors reduces tumour growth (Lancet 339, 1154–1156 [1992]). The compounds of formula I according to the invention are therefore potentially suitable for treating tumour diseases on account of their inhibitory effect on cholesterol biosynthesis. They may be used on their own or to back up known types of therapy.

Other examples include hyperproliferative skin diseases such as psoriasis, basal cell carcinomas, plate epithelial carcinomas, keratosis and keratinising disorders. The term "psoriasis" used here refers to a hyperproliferative inflammatory skin disease which changes the regulating mechanism of the skin. In particular, lesions are formed which contain primary and secondary changes in the proliferation in the epidermis, inflammatory reactions of the skin and the expression of regulatory molecules such as lymphokines and inflammatory factors. Psoriatic skin is morphologically characterised by an increased turnover of epidermis cells, a thickened epidermis, abnormal keratinisation of inflammatory cell infiltrates into the dermis layer and polymorphonuclear leukocyte infiltration into the epidermis, causing an increase in the basal cell cycle. In addition, hyperkeratotic and parakeratotic cells are present. The term "keratosis", "basal cell carcinoma", "plate epithelial carcinoma" and "keratinising disorders" refer to hyperproliferative skin diseases in which the regulating mechanism for the proliferation and differentiation of the skin cells has broken down.

The compounds of formula I are effective as antagonists of skin hyperproliferation, i.e. as agents which inhibit the hyperproliferation of human keratinocytes. The compounds are therefore suitable as agents for treating hyperproliferative skin diseases such as psoriasis, basal cell carcinomas, keratinising disorders and keratosis. In order to treat these diseases the compounds of formula I may be administered either orally or topically, and may be used either on their own as a monotherapy or combined with known active substances.

Hyperproliferative vascular diseases such as stenoses triggered by surgical procedures such as PTCA (percutaneous transluminal coronary angioplasty) or by-pass operations, and vascular blockages caused by the proliferation of smooth muscle cells should also be mentioned. As stated above, this cell proliferation can be suppressed by HMG-CoA-reductase inhibitors of the mevinolin type such as lovastatin, as is well known. In view of their inhibitory effect on cholesterol biosynthesis, the compounds of general formula I are also suitable for the treatment and prevention of these diseases, and may be used either on their own or combined with known active substances such as intravenously administered heparin, and are preferably administered orally.

Another possible use for the compounds of general formula I according to the invention is the prevention and treatment of gallstones. Gallstone-formation is triggered when the cholesterol concentration in the bile exceeds the maximum solubility of cholesterol in the bile fluid, resulting in the precipitation of cholesterol in the form of gallstones. Lipid lowering compounds from the fibrate category result in an increased precipitation of the neutral steroids through the bile and increase the tendency to gallstone formation.

By contrast, cholesterol biosynthesis inhibitors such as lovastatin or pravastatin do not cause any increase in gallstone formation but on the contrary bring about a reduction in the cholesterol concentration in the bile and thereby lower the so-called lithogenic index, which is a measurement of the probability of gallstone formation. This is described in Gut 31, 348–350 [1990] and in Z. Gastroenterol. 29, 242–245 [1991].

Moreover, Gastroenterology 102, No. 4, Pt. 2, A 319 [1992] describes the effectiveness of lovastatin in breaking up gallstones, particularly in cojunction with ursodeoxycholic acid. Because of their method of acting, the compounds of general formula I aresuitablore also suitable for the prevention and treatment of gallstones. They may be used either on their own or combined with known therapies such as, for example, treatment with ursodeoxycholic acid or shock wave lithotripsy and are preferably administered orally.

Finally, the compounds of general formula I are suitable for treating infections by pathogenic fungi such as, for example, Candida albicans, Aspergillus niger, Trichophyton mentagrophytes, Penicillium sp., Cladosporium sp. and others. As already mentioned above the end product of sterol biosynthesis in the fungal organism is not cholesterol but ergosterol which is essential for the integrity and function-of fungal cell membranes. Inhibition of ergosterol biosynthesis therefore leads to growth disorders and possibly to the killing of the fungal organisms.

For treating mycoses, the compounds of general formula I may be administered either orally or topically. They may be used either on their own or in conjunction with known antimycotic substances, particularly those which intervene in other stages of sterol biosynthesis, such as the squalene epoxidase inhibitors terbinafin and naftifin or the lanosterol-14α-demethylase inhibitors of the azole type such as ketoconazol and fluconazol.

Another possible use for the compounds of general formula I is their application to poultry rearing. Lowering the cholesterol content of eggs by administering the HMG-CoA-reductase inhibitor lovastatin to laying hens has been described (FASEB Journal 4, A 533, Abstracts 1543 [1990]). The production of low-cholesterol eggs is of interest because the cholesterol load of the body can be reduced by the use of eggs with a reduced cholesterol content without having to change eating habits. Because of their inhibitory effect on cholesterol biosynthesis, the compounds of general formula I may also be used in poultry rearing for the production of low cholesterol eggs, the substances preferably being administered as a feed additive.

The biological activity of compounds of general formula I was determined using the following methods:

I. Measuring the inhibition of $^{14}C$-acetate incorporation into the steroids which can be precipitated with digitonin: Method Human hepatoma cells (HEP-G2) are cultured for 3 days and stimulated for 16 hours in a cholesterol-free medium. The test substances (dissolved in dimethylsulphoxide, final concentration 0.1%) are added during this stimulation phase. Then after the addition of 200 $\mu$Mol/l of 2-$^{14}C$-acetate incubation is continued for a further two hours at 37° C. in the incubator.

After the detachment of the cells and saponification of the sterol esters, after extraction, sterols are precipitated using digitonin. The $^{14}C$-acetate incorporated in digitonin-precipitable sterols is determined by scintillation measurement.

The inhibitory effect was investigated at test concentrations of $10^{-7}$ Mol/l and $10^{-8}$ Mol/l. For example, the test results of the following compounds (1) to (5) of general formula I at these test concentrations are given:

(1) 6-(2-Dimethylamino-ethoxy)-2-(4-fluorobenzyl)-benzothiazole,
(2) 6-(2-Diethylamino-ethoxy)-2-(1-methylpyrrolyl-3-methyl)-benzothiazole,
(3) 6-[2-(N.N-Bis-(2-hydroxyethyl)amino)ethoxy]-2-(4-chlorophenylmercapto)-benzothiazole,
(4) 6-(2-Diethylamino-ethoxy)-2-(4-chlorophenoxy)-benzothiazole,
(5) 2-(4-Chlorobenzylmercapto)-6-(2-diethylamino-ethoxy)-benzothiazole,
(6) 2-(4-Chloro-N-methyl-anilino)-6-(2-diethylamino-ethoxy)-benzothiazole.

The percentages by which the above compounds inhibit the incorporation of $^{14}C$-acetate are shown in the following Table:

| Compound | $10^{-7}$ Mol/l | $10^{-8}$ Mol/l |
|---|---|---|
| (1) | −88 | −63 |
| (2) | −88 | −69 |
| (3) | −86 | −73 |
| (4) | −88 | −82 |
| (5) | −90 | −77 |
| (6) | −81 | −68 |

A comparison with the 2,3-epoxysqualene-lanosterol-cyclase inhibitor described in Example 1 of EP-0 468 457-A1 in the test model described above yields inhibitory values of 41% and 13%, respectively, for test concentrations of $10^{-5}$ and $10^{-6}$ Mol/l. This shows that the compounds according to the invention are clearly superior to those known from the literature.

For pharmaceutical use the compounds of general formula I may be incorporated in a manner known per se in the conventional pharmaceutical preparations for oral, rectal and topical use.

Formulations for oral use include, for example, plain and coated tablets and capsules. For rectal administration, suppositories are preferably used. The daily dose is between 0.1 and 200 mg for a person weighing 60 kg, but a daily dose of 1 to 100 mg for a person weighing 60 kg is preferred. The daily dose is preferably divided into 1 to 3 dosage units.

For topical application the compounds are administered in preparations which contain about 1 to 1000 mg, more particularly 10 to 300 mg of active substance per day. The daily dose is preferably divided into 1 to 3 dosage units.

Topical formulations include gels, creams, lotions, ointments, powders, aerosols and other conventional formulations for the application of therapeutic agents to the skin. The quantity of active substance for topical application is 1 to 50 mg per gram of formulation, but preferably 5 to 20 mg per gram of formulation. In addition to application to the skin the topical formulations of the present invention may also be used in the treatment of mucous membranes which are accessible to topical treatment. For example, the topical formulations may be applied to the mucous membranes of the mouth, lower colon and elsewhere.

For use in poultry rearing in order to produce low cholesterol eggs, the active substances of general formula I are given to the animals by conventional methods as an additive to appropriate feeds. The concentration of active substances in the complete feed is normally 0.01 to 1%, but preferably 0.05 to 0.5%.

The active substances may be administered to the feed as they are. Thus, the feeds for laying hens according to the invention contain in addition to the active substance and possibly a conventional vitamin/mineral mixture, maize, soyabean flour, meatmeal, edible fat and soya oil, for example. To this feed is added one of the above-mentioned compounds of formula I as active substance in a concentration of 0.01 to 1%, but preferably 0.05 to 0.5%.

The Examples which follow are intended to illustrate the invention:

Preparation of the starting compounds:

EXAMPLE A

Bis-(2-amino-5-methoxy-phenyl)-disulphide 50 g (0.277 mol) of 2-amino-6-methoxy-benzothiazole and 200 g (3.0 mol) of 85% potassium hydroxide are refluxed in 500 ml water for 24 hours. Then the mixture is cooled to 5° C. and in 30 minutes 15 ml of 35% hydrogen peroxide are added dropwise. After it has all been added, 200 ml of concentrated hydrochloric acid is added whilst cooling, whereby a yellow precipitate is formed. The mixture is stirred for a further 30 minutes, the precipitate is suction filtered, washed with water and dried in vacuo. Yield: 40 g (97.3% of theory), Melting point: 78–80° C., Mass spectrum: Calculated: m/e=308 Found: m/e=308

The following is obtained analogously to Example A:

Bis-(2-amino-5-ethoxy-phenyl)-disulphide.

EXAMPLE B

2-Amino-5-methoxy-thiophenol 34.3 g (0.19 mol) of 2-amino-6-methoxy-benzothiazole and 140 g (2.5 mol) of 85% potassium hydroxide are refluxed in 350 ml of water for 5 hours. Then the mixture is cooled and neutralised with 200 ml of concentrated hydrochloric acid. The mixture is stirred for a further 30 minutes, the precipitate formed is suction filtered, washed with water and dried in vacuo. Yield: 24.0 g (81.4% of theory). The following is obtained analogously to Example B:

2-Amino-5-ethoxy-thiophenol, from 2-amino-6-ethoxy-benzothiazole.

EXAMPLE C 2-(4-Chlorobenzyl)-6-ethoxy-benzothiazole

Method a 12.5 g (0.037 mol) of bis-(2-amino-5-ethoxy-phenyl)-disulphide and 8.1 g (0.08 mol) of triethylamine are dissolved in 250 ml methylene chloride and whilst cooling with ice a solution of 0.074 mol of 4-chlorophenylacetic acid chloride in 10 ml methylene chloride is added dropwise. The mixture is stirred for one hour at ambient temperature, then added to water and extracted with methylene chloride. The extracts are dried and evaporated down.

15.2 g (75.6% of theory) of crystalline bis-[2-(4-chlorophenylacetylamino)-5-methoxy-phenyl]disulphide are obtained.

13 g (0.02 mol) thereof are refluxed for 2 hours with 10 g of granulated zinc in 300 ml of ethanol and 30 ml of concentrated hydrochloric acid. Then the mixture is filtered and the filtrate is added to ice water. The precipitate formed is suction filtered. Yield: 6.0 g (50.8% of theory), Melting point: 87–89° C.

2-(4-chlorobenzyl)-6-ethoxy-benzothiazole

Method b

To 5.1 g (30 m mol) of 2-amino-5-ethoxy-thiophenol in 120 ml dichloroethane are added 30 mmol of freshly prepared 4-chlorophenylacetyl chloride and the mixture is heated for 90 minutes to reflux temperature. Then it is cooled, added to aqueous soda solution and extracted with dichloroethane. The extracts are dried and evaporated down. The evaporation residue is purified by column chromatography on silica gel (eluant: petroleum ether/ethyl acetate=4:1). Yield: 3.3 g (36.2% of theory), Melting point: 87–89° C.

2-(4-chlorobenzyl)-6-methoxy-benzothiazole

Method c 1.55 g (10 m mol) of 2-amino-5-methoxy-thiophenol are added to a hot (120° C.) mixture of 1.70 g (10 mmol) of 4-chloro-phenylacetic acid and 10 g of polyphosphoric acid. Then the mixture is heated for 30 minutes to 140–150° C., poured onto ice and extracted with ethyl acetate. The extracts are dried and evaporated down and the residue purified by column chromatography on silica gel (eluant: petroleum ether/ethyl acetate=3:1), Yield: 1.2 g (41.5% of theory), Melting point: 64–66° C.

The following are prepared analogously:

6-Methoxy-2-[4-(trifluoromethyl)benzyl]-benzothiazole (Method a), Yield: 92.7% of theory, Melting point: 63–64° C.

6-Ethoxy-2-[4-(trifluoromethyl)benzyl]-benzothiazole (Method a), Yield: 55.1% of theory, Melting point: 62–63° C.

6-Ethoxy-2-(4-fluorobenzyl)-benzothiazole (Method c), Yield: 20.8% of theory, oil.

2-(4-Fluorobenzyl)-6-methoxy-benzothiazole (Method a), Yield: 74.2% of theory, Melting point: 64–66° C.

2-(Cyclohexylmethyl)-6-ethoxy-benzothiazole (Method b), Yield: 29% of theory, oil.

6-Methoxy-2-(pyridyl-4-methyl)-benzothiazole (Method b; methyl 4-pyridylacetate is used), Yield: 13.8% of theory, Melting point: 69–70° C.

6-Methoxy-2-(pyridyl-2-methyl)-benzothiazole (Method b; ethyl 2-pyridylacetate is used), Yield: 19.1% of theory, oil.

6-Methoxy-2-(thienyl-2-methyl)-benzothiazole (Method a), Yield: 63.7% of theory, oil.

6-Methoxy-2-(naphthyl-2-methyl)-benzothiazole (Method a), Yield: 91.3% of theory, oil.

6-Methoxy-2-(naphthyl-1-methyl)-benzothiazole (Method a), Yield: 39.9% of theory, Melting point: 59–61° C.

2-Benzyl-6-ethoxy-benzothiazole (Method b), Yield: 46.8% of theory, oil.

6-Methoxy-2-(1-methylpyrrolyl-3-methyl)-benzothiazole (Method a), Yield: 59.7% of theory, oil.

6-Methoxy-2-(n-pentyl)-benzothiazole (Method c), Yield: 38% of theory, oil.

2-tert.Butyl-6-methoxy-benzothiazole (Method c), Yield: 18.1% of theory, oil.

6-Methoxy-2-(2-methyl-propyl)-benzothiazole (Method c), Yield: 23.5% of theory, oil.

6-Ethoxy-2-phenyl-benzothiazole (Method b), Yield: 17.6% of theory.

2-(4-chlorobenzyl)-4-methoxy-benzothiazole (from 2-amino-4-methoxy-benzothiazole using Method a), Yield: 12.5% of theory, oil.

6-Ethoxy-2-(2-phenylethenyl)-benzothiazole (Method c), Yield: 8.5% of theory, Melting point: 108–109° C.

2-(Cyclohexylmethyl)-6-methoxy-benzothiazole (Method c), Yield: 35.2% of theory, oil.

6-Methoxy-2-(2-phenylethyl)-benzothiazole (Method c), Yield: 22.7% of theory, Melting point: from 68° C.

EXAMPLE D

6-Methoxy-2-(1-methylpyrrolyl-2-methyl)-benzothiazole and 6-methoxy-2-(1-methylpyrrolyl-3-methyl)-benzothiazole a) 2-Bromomethyl-6-methoxy-benzothiazole 7.75 g (50 mmol) of 2-amino-5-methoxy-thiophenol are dissolved in 150 ml methylene chloride and 14.1 g (70 mmol) of bromoacetylbromide are added whilst cooling with ice. Then the mixture is heated for 1 hour to reflux temperature. After cooling solid potassium carbonate is added until foaming ceases, the mixture is filtered and the filtrate is evaporated down. The evaporation residue is purified by column chromatography on neutral aluminium oxide (eluant: petroleum ether/ethyl acetate=3:1). Yield: 6.8 g (52.7 of theory), Melting point: 90–91° C.

b) 6-Methoxy-2-(1-methylpyrrolyl-2-methyl)-benzothiazole (A) and 6-methoxy-2-(1-methylpyrrolyl-3-methyl)-benzothiazole (B)

To 26.3 g (0.102 mol) of 2-bromomethyl-6-methoxy-benzothiazole in 400 ml methylene chloride are added first of all 82.7 g (1.02 mol) of N-methylpyrrole followed by 20.0 g (0.15 mol) of aluminium chloride. After 16 hours' stirring at 65° C. the mixture is decomposed with water and extracted with methylene chloride. The extracts are dried, evaporated down and the evaporation residue purified by column chromatography on neutral aluminium oxide. (eluant: petroleum ether/ethyl acetate=5:1). Yield of A: 1.8 g (6.8% of theory), oil, Yield of B: 7.8 g (29.6% of theory), oil.

EXAMPLE E 2-(4-chlorobenzyl)-5-methoxy-benzothiazole a) 4-Chloro-N-(2-chloro-5-methoxy-phenyl)-phenylacetamide 5.8 g (30 mmol) of 2-chloro-5-methoxyaniline-hydrochloride are dissolved with 7.08 g (70 mmol) of triethylamine in 100 ml methylene chloride and whilst cooling with ice 5.86 g (31 mmol) of 4-chlorophenylacetyl chloride are added dropwise. After 2 hours' stirring the mixture is added to water and extracted with methylene chloride. The extracts are dried and evaporated down. The evaporation residue is recrystallised from ether/petroleum ether. Melting point: 149–151° C.

b) 4-Chloro-N-(2-chloro-5-methoxyphenyl)-phenylthioacetamide 2.25 g (7.25 mmol)) of the compound described above and 2.93 g (7.25 mmol) of Lawesson's reagent are refluxed in 75 ml of toluene for 1 hour. Then aqueous soda solution is added, the organic phase is separated off, dried and evaporated down. The evaporation residue is purified by column chromatography on silica gel (eluant: petroleum ether/ethyl acetate=3:1). Yield: 2.0 g (84.6% of theory), Melting point: 90–92° C.

c) 2-(4-chlorobenzyl)-5-methoxy-benzothiazole 6.6 g (20.2 mmol) of the compound described above are heated to 160–165° C. with 2.26 g (20.2 mmol) of potassium tert. butoxide in 100 ml of sulpholane for 8 hours. After cooling water is added and the mixture is extracted with ether. The extracts are dried and evaporated down. The evaporation residue is purified by column chromatography on neutral aluminium oxide (eluant:petroleum ether/ethyl acetate=4:1). Yield: 1.88 g (32.1% of theory), Melting point: 83–85° C.

EXAMPLE F 2-(4-chlorophenylmercapto)-6-ethoxy-benzothiazole
a) 2-Chloro-6-ethoxy-benzothiazole 20 g (0.103 mol) of 2-amino-6-ethoxy-benzothiazole are dissolved in 100 ml of glacial acetic acid and 52 ml of concentrated hydrochloric acid and whilst cooling with ice the mixture is diazotised with 7.4 g (0.108 mol) of sodium nitrite in 15 ml of water. Then the solution of the diazonium salt is added batchwise to a suspension of 13.6 g (0.137 mol) of copper-I-chloride in 65 ml of concentrated hydrochloric acid and stirred for 20 minutes at 30° C. Then the mixture is diluted with 800 ml of ice water and the crystals formed are suction filtered. To purify them they are chromatographed on silica gel (eluant: petroleum ether/ethyl acetate= 6:1). Yield: 61.7% of theory, Melting point: 60–61° C.
b) 2-(4-chlorophenylmercapto)-6-ethoxy-benzothiazole 4.5 g (21 mmol) of the product described above are stirred with 3.2 g (22 mmol) of 4-chlorothiophenol and 6.9 g (50 mmol) of potassium carbonate for 5 hours in 100 ml of dimethylformamide at 120° C. Then the mixture is added to water and extracted with ethyl acetate. The residue remaining after drying and evaporation of the extracts is purified by column chromatography on silica gel (eluant: petroleum ether/ethyl acetate=4:1). Yield: 5.9 g (87.3% of theory), Melting point: 73–74° C.

The following are obtained analogously to Example F:

6-Ethoxy-2-(4-fluorophenylmercapto)-benzothiazole, Yield: 98% of theory, Melting point: 60–61° C.

2-(4-Chloro-N-methyl-anilino)-6-ethoxy-benzothiazole (sodium hydride is used as base), Yield: 57.1% of theory, Melting point: 90–92° C.

6-Ethoxy-2-(N-methyl-anilino)-benzothiazole (sodium hydride is used as base), Yield: 27.5% of theory, oil.

6-Ethoxy-2-phenylmercapto-benzothiazole, Yield: 90.5% of theory, oil.

EXAMPLE G 2-(4-Cyanophenylmercapto)-6-ethoxy-benzothiazole 2.11 g (10 mmol) of 6-ethoxy-2-mercapto-benzothiazole are dissolved in 50 ml of dimethylformamide and after the addition of 1.33 g (11 mmol) of 4-fluorobenzonitrile and 2.76 g (20 mmol) of potassium carbonate the mixture was stirred for 2.5 hours at 140° C. Then it is added to water and extracted with ethyl acetate. The concentrated extracts are purified by column chromatography on silica gel (eluant: petroleum ether/ethyl acetate=3:1). Yield: 0.63 g (20.2% of theory), Melting point: 86–88° C.

The following are obtained analogously to Example G:

6-Ethoxy-2-(2.2-dimethyl-propylmercapto)-benzothiazole, Yield: 90.4% of theory, oil.

2-Benzylmercapto-6-ethoxy-benzothiazole, Yield: 87.9% of theory, Melting point: 61–62° C.

2-(4-chlorobenzylmercapto)-6-ethoxy-benzothiazole, Yield: 85.5% of theory, Melting point: 81–82° C.

2-tert.Butylmercapto-6-ethoxy-benzothiazole, Yield: 11.2% of theory, oil.

6-Ethoxy-2-(2-methyl-4-nitro-phenylmercapto)-benzothiazole, Yield: 91% of theory, oil.

6-Ethoxy-2-(2-phenylethylmercapto)-benzothiazole, Yield: 87% of theory, oil.

6-Ethoxy-2-(n-hexylmercapto)-benzothiazole, Yield: 65.5% of theory, oil.

6-Hydroxy-2-[(4-methyl-4-pentenyl-1)-mercapto]-benzothiazole, Yield: 35.2% of theory, oil.

6-Ethoxy-2-[4-(trifluoromethyl)phenylmercapto]-benzothiazole, Yield: 89.4% of theory.

6-Ethoxy-2-(4-nitrophenylmercapto)-benzothiazole, Yield: 70.8% of theory, Melting point: 103–104° C.

6-Ethoxy-2-(2-methyl-propylmercapto)-benzothiazole, Yield: 69.9% of theory, oil.

6-Hydroxy-2-triphenylmethylmercapto)-benzothiazole, from 6-hydroxy-2-mercapto-benzothiazole and triphenylmethyl chloride, Yield: 83.6% of theory.

EXAMPLE H 2-(4-Fluorophenylmercapto)-6-hydroxy-benzothiazole 1.17 g (3.83 mmol) of 6-ethoxy-2-(4-fluorophenylmercapto)-benzothiazole in 25 ml of methylene chloride are mixed with 2.5 g (10 mmol) of boron tribromide at 0–5° C. and stirred for 4 hours at ambient temperature. Then the mixture is poured onto aqueous soda solution and extracted with methylene chloride. The extracts are dried and evaporated down. Yield: 1.03 g (97% of theory), Melting point: 168–171° C.

The following are obtained analogously to Example H:

2-Chloro-6-hydroxy-benzothiazole, Yield:.96% of theory.

2-(4-chlorophenylmercapto)-6-hydroxy-benzothiazole, Yield: 85.4% of theory, Melting point: 177–180° C.

2-(2.2-Dimethyl-propylmercapto)-6-hydroxy-benzothiazole, Yield: 93.3% of theory, Melting point: 126–128° C.

6-Hydroxy-2-[4-(trifluoromethyl)benzylmercapto]-benzothiazole, Yield: 89.4% of theory.

6-Hydroxy-2-mercapto-benzothiazole, Yield: 62.7% of theory.

2-Benzylmercapto-6-hydroxy-benzothiazole, Yield: 87% of theory, Melting point: 154–155° C.

6-Hydroxy-2-(n-hexylmercapto)-benzothiazole, Yield: 65.5% of theory, Melting point: 90–92° C.

6-Hydroxy-2-(2-phenylethylmercapto)-benzothiazole, Yield: 87% of theory, Melting point: 123–124° C.

6-Hydroxy-2-(2-methyl-propylmercapto)-benzothiazole, Yield: 69.9% of theory, Melting point: 173–175° C.

2-(4-chlorobenzylmercapto)-6-hydroxy-benzothiazole, Yield: 30% of theory, Melting point: 160–162° C.

6-Hydroxy-2-(2-methyl-4-nitro-phenylmercapto)-benzothiazole, Yield: 89% of theory, Melting point: 220–225° C.

6-Hydroxy-2-phenylmercapto-benzothiazole, Yield: 92% of theory, Melting point: amorphous.

2-(4-Cyanophenylmercapto)-6-hydroxy-benzothiazole, Yield: 31.1% of theory.

6-Hydroxy-2-(4-nitrophenylmercapto)-benzothiazole, Yield: 81.6% of theory, Melting point: 200–201° C.

6-Hydroxy-2-(N-methyl-anilino)-benzothiazole, Yield: 87% of theory.

2-(4-Chloro-N-methyl-anilino)-6-hydroxy-benzothiazole, Yield: 58.9% of theory, Melting point: amorphous.

6-Hydroxy-2-(2-phenylethenyl)-benzothiazole, Yield: 78.9% of theory, Melting point: 223–225° C.

2-(4-chlorobenzyl)-6-hydroxy-benzothiazole, Yield: 43.7% of theory, Melting point: 173–175° C.

2-Benzyl-6-hydroxy-benzothiazole, Yield: 91% of theory.

6-Hydroxy-2-[4-(trifluoromethyl)benzyl]-benzothiazole, Yield: 80.2% of theory, Melting point: 152–154° C.

2-Cyclohexylmethyl-6-hydroxy-benzothiazole, Yield: 81.2% of theory, Melting point: 164–165° C.

6-Hydroxy-2-(n-pentyl)-benzothiazole, Yield: 83.2% of theory, Melting point: 92–93° C.

6-Hydroxy-2-(2-methyl-propyl)-benzothiazole, Yield: 58.1% of theory, Melting point: 140–142° C.

2-tert.Butyl-6-hydroxy-benzothiazole, Yield: 72.5% of theory, Melting point: 175–178° C.

2-(4-Fluorobenzyl)-6-hydroxy-benzothiazole, Yield: 67% of theory, Melting point: 164–166° C.

2-(2-Phenylethyl)-6-hydroxy-benzothiazole, Yield: 60% of theory, Melting point: 170–172° C.

2-(4-chlorobenzyl)-4-hydroxy-benzothiazole, Yield: 90.7% of theory, Melting point: 127–130° C.

2-(4-chlorobenzyl)-5-hydroxy-benzothiazole, Yield: 50.6% of theory, Melting point: 112–113° C.

EXAMPLE I

6-Hydroxy-2-(pyridyl-2-methyl)-benzothiazole 0.95 g (3.7 mmol) of 6-methoxy-2-(pyridyl-2-methyl)-benzothiazole and 9.5 g of pyridine hydrochloride are stirred for 2 hours at 180° C. Then the mixture is added to water, saturated with sodium chloride and extracted with ethyl acetate. The extracts are dried and evaporated down. Purification is achieved by chromatography on silica gel (eluant: ethyl acetate). Yield: 0.52 g (58.0% of theory), Melting point: 122–124° C.

The following are obtained analogously to Example I:

6-Hydroxy-2-(pyridyl-4-methyl)-benzothiazole, Yield: 30.4% of theory, Melting point: 196–199° C.

6-Hydroxy-2-(1-methylpyrrolyl-3-methyl)-benzothiazole, Yield: 26.6% of theory, Melting point: 159–161° C.

6-Hydroxy-2-(thienyl-2-methyl)-benzothiazole, Yield: 71.0% of theory, Melting point: 146–149° C.

2-(4-Fluorobenzyl)-6-hydroxy-benzothiazole, Yield: 91.7% of theory, Melting point: 166° C.

EXAMPLE K

6-Hydroxy-2-(naphthyl-2-methyl)-benzothiazole 0.97 g (3.18 mmol) of 6-Methoxy-2-(naphthyl-2-methyl)-benzothiazole are dissolved in 30 ml of toluene and after the addition of 0.85 g (6.4 mmol) of aluminium chloride the mixture is stirred for 90 minutes at 80° C. It is then added to ice/hydrochloric acid and extracted with ethyl acetate. The extracts are dried and evaporated down. The evaporation residue is digested with diisopropyl ether and the crystals are suction filtered. Yield: 0.6 g (64.8% of theory), Melting point: 152–154° C.

The following are obtained analogously:

6-Hydroxy-2-(naphthyl-1-methyl)-benzothiazole, Yield: 91.5% of theory, Melting point: 176–178° C.

6-Hydroxy-2-(1-methylpyrrolyl-2-methyl)-benzothiazole and 6-hydroxy-2-(1-methylpyrrolyl-3-methyl)-benzothiazole, prepared as a mixture from the mixture of the corresponding 6-methoxy compounds, Yield: 47.4% of theory.

EXAMPLE L

2-Benzylsulphonyl-6-hydroxy-benzothiazole 0.45 g (2 mmol) of 2-benzylmercapto-6-hydroxy-benzothiazole are dissolved in 15 ml of warm glacial acetic acid and at 50° C. 2.5 ml of 35% hydrogen peroxide is added. The mixture is stirred for 1 hour at 50° C. and 20 minutes at 100° C. It is then added to water, neutralised with soda and extracted with ethyl acetate. The extracts are dried and evaporated down. The evaporation residue is digested with a little ether and suction filtered. Yield: 60.6% of theory, Melting point: 188–189° C.

EXAMPLE M 2-(4-chlorobenzyl)-6-hydroxy-benzoxazole a) 4-Chloro-N-(2,4-dimethoxy-phenyl)-phenylacetamide To 3.56 g (20 mmol) of 2,4-dimethoxyaniline and 2.53 g (25 mmol) of triethylamine in 50 ml of methylene chloride are added dropwise, whilst cooling with ice, 3.97 g (21 mmol) of 4-chlorophenylacetyl chloride. The mixture is stirred for a further hour at ambient temperature, added to dilute hydrochloric acid and extracted with methylene chloride. The extracts are dried and evaporated down. The evaporation residue is triturated with petroleum ether and suction filtered. Yield: 5.2 g (85.0% of theory), Melting point: 134–135° C.

b) 4-Chloro-N-(2,4-dihydroxy-phenyl)-phenylacetamide

Prepared by ether splitting the above compound with boron tribromide analogously to Example H. Yield: 93% of theory, Melting point: 178–179° C.

c) 2-(4-chlorobenzyl)-6-hydroxy-benzoxazole 1.5 g (5.4 mmol) of the above compound is dissolved in 20 ml of glycoldimethylether and after the addition of 150 mg of p-toluenesulphonic acid the mixture was refluxed for 2 hours. Then it was added to water and the precipitate formed was suction filtered. Yield: 0.65 g (46% of theory), Melting point: 167–168° C.

EXAMPLE N 6-(2-Bromoethoxy)-2-(4-fluorobenzyl)-benzothiazole 2.9 g (11 mmol) of 2-(4-fluorobenzyl)-6-hydroxy-benzothiazole are dissolved in 50 ml of absolute tetrahydrofuran. 1.9 g (15 mmol) of 2-bromoethanol and 4.0 g (15 mmol) of triphenylphosphine are added successively and then at ambient temperature 2.6 g (15 mmol) of diethyl azodicarboxylate are added dropwise. After stirring overnight the mixture is evaporated down and purified by column chromatography on silica gel (eluant: petroleum ether/ethyl acetate=3:1). Yield: 65.5% of theory, Melting point: 108–110° C.

The following are prepared analogously:

6-(2-Bromoethoxy)-2-(4-chlorobenzyl)-benzothiazole, Yield: 75.6% of theory, Melting point: 105–107° C.

6-(2-Bromoethoxy)-2-[4-(trifluoromoethyl)benzyl]-benzothiazole, Yield: 55.9% of theory, Melting point: 102–103° C.

6-(2-Bromoethoxy)-2-(4-fluorophenylmercapto)-benzothiazole, Yield: 83.1% of theory, Melting point: 98–100° C.

6-(2-Bromoethoxy)-2-(4-chlorophenylmercapto)-benzothiazole, Yield: 75% of theory, Melting point: 85–87° C.

6-(2-Bromoethoxy)-2-(4-chlorobenzyl)-benzoxazole, Yield: 88.4% of theory, Melting point: 58–60° C.

5-(2-Bromoethoxy)-2-(4-chlorobenzyl)-benzothiazole, Yield: 61.5% of theory, Melting point: 93–94° C.

6-(2-Bromoethoxy)-2-(naphthyl-2-methyl)-benzothiazole, Yield: 77.7% of theory, Melting point: 107–109° C.

6-(2-Bromoethoxy)-2-(naphthyl-1-methyl)-benzothiazole, Yield: 56.6% of theory, Melting point: 117–118° C.

6-(2-Bromoethoxy)-2-(thienyl-2-methyl)-benzothiazole, Yield: 74.6% of theory, Melting point: 79–80° C.

6-(2-Bromoethoxy)-2-(pyridyl-2-methyl)-benzothiazole, Yield: 93% of theory, oil.

6-(2-Bromoethoxy)-2-(pyridyl-4-methyl)-benzothiazole, Yield: 66.4% of theory.

2-tert.Butyl-6-(2-bromoethoxy)-benzothiazole, Yield: 78.5% of theory, oil.

6-(2-Bromoethoxy)-2-(n-pentyl)-benzothiazole, Yield: 19.2% of theory, Melting point: 48–50° C.

6-(2-Bromoethoxy)-2-cyclohexylmethyl-benzothiazole, Yield: 65.7% of theory, Melting point: 50–53° C.

EXAMPLE O 6-(2-Bromoethoxy)-2-(4-chlorobenzyl)-benzothiazole a) 2-(4-chlorobenzyl)-6-(2-hydroxyethoxy)-benzothiazole 1.05 g (3.8 mmol) of 2-(4-chlorobenzyl)-6-hydroxy-benzothiazole and 0.67 g (7.6 mmol) of ethylene carbonate are dissolved in 20 ml of dimethylformamide and after the addition of 2.1 g (15.2 mmol) of potassium carbonate the mixture is stirred for 2 hours at 120° C. It is then added to water and extracted with ethyl acetate. After the extracts have been evaporated down the residue is purified by column chromatography on silica gel (eluant: ethyl acetate). Yield: 1.6 g (69% of theory).

b.) 6-(2-Bromoethoxy)-2-(4-chlorobenzyl)-benzothiazole 1.6 g (5.0 mmol) of the compound described above are dissolved in 25 ml of methylene chloride and after the addition of 1.45 g (5.5 mmol) of triphenylphosphine and 1.83 g (5.5 mmol) of tetrabromomethane the mixture is stirred for 3 hours at ambient temperature. It is then evaporated down and the evaporation residue purified by column chromatography on silica gel (eluant: petroleum ether/methyl acetate=4:1). Yield: 4.47 g (77.3% of theory), Melting point: 106° C.

The following are obtained analogously to Example O:

6-(2-Bromoethoxy)-2-(4-chlorobenzylmercapto)-benzothiazole, Yield: 51.4% of theory, Melting point: 91–92° C.

6-(2-Bromoethoxy)-2-(4-chlorophenylmercapto)-benzothiazole, Yield: 58.6% of theory, Melting point: 106–108° C.

EXAMPLE P 6-(4-Bromobutyloxy)-2-(4-chlorophenylmercapto)-benzothiazole 0.74 g (2.5 mmol) of 6-hydroxy-2-(4-chlorophenylmercapto)-benzothiazole are dissolved in 20 ml of dimethylformamide and after the addition of 2.16 g (10 mmol) of 1.4-dibromobutane and 2.07 g (15 mmol) of potassium carbonate the resulting mixture is stirred for 20 hours at ambient temperature. The mixture is then added to water and extracted with ethyl acetate. The extracts are dried and evaporated down. The evaporation residue is purified by column chromatography on silica gel (eluant: petroleum ether/ethyl acetate=4:1). Yield: 0.85 g (79.3% of theory), oil.

The following are obtained analogously to Example P:

6-(4-Bromobutyloxy)-2-(4-chlorobenzylmercapto)-benzothiazole, Yield:-90.3% of theory, Melting point: 69–71° C.

6-(6-Bromohexyloxy)-2-(4-chlorobenzyl)-benzothiazole, Yield: 60% of theory, Melting point: 65° C.

6-(4-Bromobutyloxy)-2-(4-chlorobenzyl)-benzothiazole, Yield: 93% of theory, oil.

Preparation of the end products:

EXAMPLE 1

2-(2-chlorophenylmercapto)-6-(2-diethylamino-ethoxy)-benzothiazole a) 2-Chloro-6-(2-diethylamino-ethoxy)-benzothiazole 3.15 g (16.7 mmol) of 2-chloro-6-hydroxy-benzothiazole are dissolved in 50 ml of dimethylformamide and after the addition of 5.68 g (33 mmol) of 2-diethylamino-ethyl chloride-hydrochloride and 8.3 g (60 mmol) of potassium carbonate the mixture was stirred for 20 hours at ambient temperature. It was then added to water and extracted with ethyl acetate. The extracts are dried and evaporated down. The evaporation residue is purified by column chromatography on neutral aluminium oxide (eluant: petroleum ether/ethyl acetate=6:1). Yield: 3.9 g (81.7% of theory), oil, $^1$H-NMR spectrum (200 MHz, CDCl$_3$, signals at ppm): 1.08 (t, 6H); 2.65 (q, 4H); 2.9 (t, 2H); 4.09 (t, 2H); 7.08 (dd, 1H); 7.24 (d, 1H); 7.8 (d, 1H).

b) 2-(2-chlorophenylmercapto)-6-(2-diethylamino-ethoxy)-benzothiazole 0.43 g (1.5 mmol) of the compound described above are dissolved in 25 ml of dimethylformamide and after the addition of 0.29 g (2 mmol) of 2-chloro-thiophenol and 0.69 g (5 mmol) of potassium carbonate the mixture is stirred for 2 hours at 120° C. Then it is worked up as before. Yield: 0.55 g (93.3% of theory), oil, $^1$H-NMR spectrum (200 MHz, CDCl$_3$, signals at ppm): 1.06 (t, 6H); 2.62 (q, 4H); 2.88 (t, 2H); 4.06 (t, 2H); 7.04 (dd, 1H); 7.18 (d, 1H); 7.23–7.46 (m, 2H); 7.55 (dd, 1H); 7.71 (dd, 1H); 7.8 (dd, 1H).

The following are obtained analogously to Example 1:

2-(4-chlorophenylmercapto)-6-(2-diethylamino-ethoxy)-benzothiazole, Yield: 81.4% of theory, oil, $^1$H-NMR spectrum (200 MHz, CDCl$_3$, signals at ppm): 1.06 (t, 6H); 2.63(q, 4H); 2.87 (t, 2H); 4.05 (t, 2H); 7.02 (dd, 1H); 7.17 (d, 1H); 7.42 (d, 2H); 7.63 (d, 2H); 7.78 (d, 1H).

6-(2-Diethylamino-ethoxy)-2-(4-methylphenylmercapto)-benzothiazole, Yield: 93% of theory, oil, $^1$H-NMR spectrum (200 MHz, CDCl$_3$, signals at ppm): 1.05 (t, 6H); 2.43 (s, 3H); 2.62 (q, 4H); 2.87 (t, 2H); 4.03 (t, 2H); 7.0 (dd, 1H); 7.12 (d, 1H); 7.27 (d, 2H); 7.6 (d, 2H); 7.75 (d, 1H).

6-(2-Diethylamino-ethoxy)-2-(4-methyl-phenylsulphonyl)-benzothiazole, from 2-chloro-6-(2-diethylamino-ethoxy)-benzothiazole and the sodium salt of 4-methylphenylsulphinic acid, Yield::95.7% of theory, oil, $^1$H-NMR spectrum (200 MHz, CDCl$_3$, signals at ppm): 1.06 (t, 6H); 2.42 (s, 3H); 2.64 (q, 4H); 2.9 (t, 2H); 4.1 (t, 2H); 7.16 (dd, 1H); 7.33 (d, 1H); 7.36 (d, 2H); 8.0 (m, 3H).

6-(2-Diethylamino-ethoxy)-2-phenoxy-benzothiazole, from 2-chloro-6-(2-diethylamino-ethoxy)-benzothiazole and phenol in the presence of potassium tert. butoxide, Yield: 85.5% of theory, oil, $^1$H-NMR spectrum (200 MHz, CDCl$_3$, signals at ppm): 1.08 (t, 6H); 2.65 (q, 4H); 2.88 (t, 2H); 4.06 (t, 2H); 6.99 (dd, 1H); 7.18 (d, 1H); 7.22–7.51 (m, 5H); 7.62 (d, 1H).

2-tert.Butylmercapto-6-(2-diethylamino-ethoxy)-benzothiazole, Yield: 57% of theory, oil, $^1$H-NMR spectrum (200 MHz, DMSO-d$_6$, signals at ppm): 0.98 (t, 6H); 1.52 (s, 9H); 2.56 (q, 4H); 2.8 (t, 2H); 4.08 (t, 2H); 7.09 (dd, 1H); 7.62 (d, 1H); 7.86 (d, 1H).

6-(2-Diethylamino-ethoxy)-2-(4-fluorophenylmercapto)-benzothiazole, Yield: 93.7% of theory, oil, $^1$H-NMR spectrum (200 MHz, DMSO-d$_6$, signals at ppm): 0.95 (t, 6H); 2.54 (q, 4H); 2.77 (t, 2H); 4.03 (t, 2H); 7.04 (dd, 1H); 7.21–7.5 (m, 2H); 7.54 (d, 1H); 7.73 (d, 1H); 7.79–7.92 (m, 2H).

6-(2-Diethylamino-ethoxy)-2-(pyridyl-2-mercapto)-benzothiazole, Yield: 94.4% of theory, oil, $^1$H-NMR spectrum (200 MHz, DMSO-d$_6$, signals at ppm): 0.98 (t, 6H); 2.55 (q, 4H); 2.81 (t, 2H); 4.09 (t, 2H); 7.11 (dd, 1H); 7.34–7.46 (m, 1H); 7.58–7.71 (m, 2H); 7.8–7.95 (m, 2H); 8.6 (dd, 1H).

2-(4-(Chlorophenoxy)-6-(2-diethylamino-ethoxy)-benzothiazole, from 2-chloro-6-(2-diethylamino-ethoxy)-benzothiazole and 4-chlorophenol in the presence of potassium tert. butoxide, Yield: 63.7% of theory, Melting point: 60–62° C., $^1$H-NMR spectrum (200 MHz, DMSO-d$_6$, signals at ppm): 0.98 (t, 6H); 2.55 (q, 4H); 2.78 (t, 2H); 4.04 (t, 2H); 7.02 (dd, 1H); 7.41–7.64 (m, 6H).

6-(2-Diethylamino-ethoxy)-2-(pyridyl-4-mercapto)-benzothiazole, Yield: 88.9% of theory, oil, $^1$H-NMR spectrum (200 MHz, DMSO-d$_6$, signals at ppm): 1.08 (t, 6H); 2.55 (q, 4H); 2.81 (t, 2H); 4.09 (t, 2H); 7.14 (dd, 1H); 7.54 (d, 2H); 7.7 (d, 1H); 7.91 (d, 1H); 8.58 (d, 2H).

EXAMPLE 2

2-(4-chlorophenylmercapto)-6-(3-diethylamino-propoxy)-benzothiazole 0.59 g (2 mmol) of 2-(4-chlorophenylmercapto)-6-hydroxy-benzothiazole and 0.74 g (4 mmol) of 3-diethylaminopropyl chloride-hydrochloride are suspended in 20 ml of dimethylformamide and after the addition of 1.38 g (10 mmol) of potassium carbonate the mixture is stirred for 4 hours at 80° C. It is then added to water and extracted with ethyl acetate. The extracts are dried and evaporated down and the evaporation residue is purified by column chromatography on neutral aluminium oxide. Yield: 0.66 g (81.1% of theory), oil, $^1$H-NMR spectrum (200 MHz, DMSO-d$_6$, signals at ppm): 0.92 (t, 6H); 1.8 (m, 2H); 2.35–2.58 (q+t, 6H); 4.02 (t, 2H); 7.07 (dd, 1H); 7.54 (d, 1H); 7.62 (d, 2H); 7.7–7.85 (m, 3H).

The following are prepared analogously:

2-(4-chlorophenylmercapto)-6-[2-(morpholinyl-1)ethoxy]-benzothiazole, Yield: 76.2% of theory, Melting point: 91–92° C., $^1$H-NMR spectrum (200 MHz, DMSO-d$_6$, signals at ppm): 2.48 (t, 4H); 2.7 (t, 2H); 3.56 (t, 4H); 4.1 (t, 2H); 7.08 (dd, 1H); 7.52–7.85 (2m, 6H).

2-(4-chlorophenylmercapto)-6-(2-diethylamino-ethoxy)-benzothiazole, Yield: 84.3% of theory, oil, $^1$H-NMR spectrum (200 MHz, CDCl$_3$, signals at ppm): 1.06 (t, 6H); 2.63 (q, 4H); 2.87 (t, 2H); 4.05 (t, 2H); 7.02 (dd, 1H); 7.17 (d, 1H); 7.42 (d, 2H); 7.63 (d, 2H); 7.78 (d, 1H).

6-(2-Diethylamino-ethoxy)-2-phenylmercapto-benzothiazole, Yield: 77.3% of theory, oil, $^1$H-NMR spectrum (200 MHZ, CDCl$_3$, signals at ppm): 1.05 (t, 6H); 2.62 (q, 4H); 2.87 (t, 2H); 4.04 (t, 2H); 7.0 (dd, 1H); 7.14 (d, 1H); 7.45 (m, 3H); 7.7 (m, 2H); 7.77 (d, 1H).

6-(2-Diethylamino-ethoxy)-2-[(2-methyl-4-nitro-phenyl)mercapto]-benzothiazole, Yield: 64.7% of theory, oil, $^1$H-NMR spectrum (200 MHz, CDCl$_3$/CD$_3$OD, signals at ppm): 1.09 (t, 6H); 2.58 (s, 3H); 2.67 (q, 4H); 2.93 (t, 2H); 4.11 (t, 2H); 7.1 (dd,1H); 7.29 (d,1H); 7.69 (d, 1H); 7.84 (d, 1H); 8.07 (dd, 1H); 8.2 (d, 1H).

2-Benzylmercapto-6-(2-diethylamino-ethoxy)-benzothiazole, Yield: 75.2% of theory, oil, $^1$H-NMR spectrum (200 MHz, CDCl$_3$, signals at ppm): 1.08 (t, 6H); 2.64 (q, 4H); 2.90 (t, 2H); 4.08 (t, 2H); 4.56 (s, 2H); 7.02 (dd, 1H); 7.2–7.49 (m, 6H); 7.78 (d, 1H).

2-(4-chlorobenzylmercapto)-6-(2-diethylamino-ethoxy)-benzothiazole, Yield: 61.4% of theory, oil, $^1$H-NMR spectrum (200 MHz, CDCl$_3$, signals at ppm): 1.08 (t, 6H); 2.64 (q, 4H); 2.90 (t, 2H); 4.08 (t, 2H); 4.51 (s, 2H); 7.02 (dd, 1H); 7.22 (d, 1H); 7.32 (AB, 4H); 7.78 (d, 1H).

2-(4-chlorobenzylmercapto)-6-(3-diethylamino-propoxy)-benzothiazole, Yield: 86.9% of theory, oil, $^1$H-NMR spectrum (200 MHz, CDCl$_3$, signals at ppm): 1.04 (t, 6H); 1.95 (m, 2H); 2.55 (q, 4H); 2.60 (m, 2H); 4.05 (t, 2H); 4.51 (s, 2H); 7.02 (dd, 1H); 7.22 (d, 1H); 7.32 (AB, 4H); 7.78 (d, 1H).

2-(4-chlorobenzylmercapto)-6-[2-(piperidinyl-1)ethoxy]-benzothiazole, Yield: 90.7% of theory, oil, $^1$H-NMR spectrum (200 MHz, CDCl$_3$, signals at ppm): 1.38–1.73 (2m, 6H); 2.51 (bm, 4H); 2.8 (t, 2H); 4.15 (t, 2H); 4.51 (s, 2H); 7.04 (dd, 1H); 7.23 (d, 1H); 7.33 (AB, 4H); 7.78 (d, 1H).

2-(4-chlorobenzylmercapto)-6-[2-(pyrrolidinyl-1)ethoxy]-benzothiazole, Yield: 86.4% of theory, oil, $^1$H-NMR spectrum (200 MHz, CDCl$_3$, signals at ppm): 1.8 (bm, 4H); 2.62 (bm, 4H); 2.92 (t, 2H); 4.14 (t, 2H); 4.50 (s, 2H); 7.05 (dd, 1H); 7.24 (d, 1H); 7.32 (AB, 4H); 7.78 (d, 1H).

2-(4-chlorobenzylmercapto)-6-(2-dimethylamino-ethoxy)-benzothiazole, Yield: 37% of theory, Melting point: 55–58° C., $^1$H-NMR spectrum (200 MHz, CDCl$_3$, signals at ppm): 2.35 (s, 6H); 2.75 (t, 2H); 4.1 (t, 2H); 4.51 (s, 2H); 7.06 (dd, 1H); 7.24 (d, 1H); 7.32 (AB, 4H); 7.77 (d, 1H).

2-(4-Cyanophenylmercapto)-6-(2-diethylamino-ethoxy)-benzo-thiazole, Yield: 47.8% of theory, oil, $^1$H-NMR spectrum (200 MHz, CDCl$_3$, signals at ppm): 1.08 (t, 6H); 2.65 (q, 4H); 2.90 (t, 2H); 4.09 (t, 2H); 7.1 (dd, 1H); 7.25 (d, 1H); 7.65 (s, 4H); 7.87 (d, 1H).

6-(2-Diethylamino-ethoxy)-2-(4-nitrophenylmercapto)-benzo-thiazole, Yield: 91.3% of theory, oil, $^1$H-NMR spectrum (200 MHz, CDCl$_3$, signals at ppm): 1.07 (t, 6H); 2.65 (q, 4H); 2.90 (t, 2H); 4.09 (t, 2H); 7.1 (dd, 1H); 7.27 (d, 1H); 7.68 (d, 2H); 7.89 (d, 1H); 8.22 (d, 2H).

6-(2-Diethylamino-ethoxy)-2-(2,2-dimethyl-propylmercapto)-benzothiazole, Yield: 75.6% of theory, oil, $^1$H-NMR spectrum (200 MHz, CDCl$_3$, signals at ppm): 1.07 (t+s, 15H); 2.65 (q, 4H); 2.90 (t, 2H); 3.34 (s, 2H); 4.08 (t, 2H); 7.00 (dd, 1H); 7.22 (d, 1H); 7.72 (d, 1H).

6-(2-Diisopropylamino-ethoxy)-2-(2,2-dimethyl-propylmercapto)-benzothiazole, Yield: 88.8% of theory, oil, $^1$H-NMR spectrum (200 MHz, CDCl$_3$, signals at ppm): 0.95–1.13 (m, 21H); 2.85 (t, 2H); 3.05 (m, 2H); 3.34 (s, 2H); 3.92 (t, 2H); 6.99 (dd, 1H); 7.22 (d, 1H); 7.73 (d, 1H).

2-(2-Methyl-propylmercapto)-6-(2-diethylamino-ethoxy)-benzothiazole, Yield: 88.5% of theory, oil, $^1$H-NMR spectrum (200 MHz, CDCl$_3$, signals at ppm): 1.06 (m, 12H); 2.07 (m, 1H); 2.64 (m, 4H); 2.90 (t, 2H); 3.21 (d, 2H); 4.08 (t, 2H); 7.0 (dd, 1H); 7.23 (d, 1H); 7.73 (d, 1H); Hydrochloride (from ether): Melting point: 131–133° C.

6-(2-Diethylamino-ethoxy)-2-(n-hexylmercapto)-benzothiazole, Yield: 87.3% of theory, oil, $^1$H-NMR spectrum (200 MHz, CDCl$_3$, signals at ppm): 0.9 (m, 3H); 1.08 (t, 6H); 1.2–1.6 (m, 6H); 1.7–1.9 (m, 2H); 2.64 (q, 4H); 2.9 (t, 2H); 3.3 (t, 2H); 4.08 (t, 2H); 7.01 (dd, 1H); 7.23 (d, 1H); 7.74 (d, 1H).

6-(2-Diethylamino-ethoxy)-2-(2-phenylethylmercapto)-benzo-thiazole, Yield: 90.5% of theory, oil. $^1$H-NMR spectrum (200 MHz, CDCl$_3$, signals at ppm): 1.08 (t, 6H); 2.65 (q, 4H); 2.90 (t, 2H); 3.12 (t, 2H); 3.55 (t, 2H); 4.09 (t, 2H); 7.03 (dd, 1H); 7.18–7.40 (m, 6H); 7.76 (d, 1H).

6-(2-Diethylamino-ethoxy)-2-triphenylmethylmercapto-benzo-thiazole, Yield: 39.0% of theory, oil, $^1$H-NMR spectrum (200 MHz, CDCl$_3$, signals at ppm): 1.03 (t, 6H); 2.59 (q, 4H); 2.84 (t, 2H); 3.85 (t, 2H); 6.79 (dd, 1H); 6.97 (d, 1H); 7.15–7.55 (m, 16H).

6-(2-Diethylamino-ethoxy)-2-[(4-methyl-4-pentenyl-1)mercapto]-benzothiazole, Yield: 94.6% of theory, oil, $^1$H-NMR spectrum (200 MHz, CDCl$_3$, signals at ppm): 1.07 (t, 6H); 1.65 (s, 3H); 1.71 (s, 3H); 2.50 (m, 2H); 2.65 (q, 4H); 2.90 (t, 2H); 3.30 (t, 2H); 4.08 (t, 2H); 5.21 (t, 1H); 7.0 (dd, 1H); 7.24 (d, 1H); 7.73 (d, 1H1).

6-(2-Diethylamino-ethoxy)-2-benzylsulphonyl-benzothiazole, Yield: 89.2% of theory, waxy, $^1$H-NMR spectrum (200 MHz, CDCl$_3$, signals at ppm): 1.08 (t, 6H); 2.66 (q, 4H); 2.93 (t, 2H); 4.11 (t, 2H); 4.71 (s, 2H); 7.16–7.40 (m, 7H); 8.10 (d, 1H).

2-(4-Chloro-N-methyl-anilino)-6-(2-diethylamino-ethoxy)-benzothiazole, Yield: 68.4% of theory, oil, $^1$H-NMR spectrum (200 MHz, DMSO-d$_6$, signals at ppm): 0.95 (t, 6H); 2.54 (q, 4H); 2.76 (t, 2H); 3.51 (s, 3H); 3.98 (t, 2H); 6.9 (dd, 1H); 7.36 (d, 1H); 7.44 (d, 1H); 7.56 (s, 4H).

6-(2-Diethylamino-ethoxy)-2-(N-methyl-anilino)-benzothiazole, Yield: 17% of theory, oil, $^1$H-NMR spectrum (200 MHz, CDCl$_3$/CD$_3$OD, signals at ppm): 1.09 (t, 6H); 2.65 (q, 4H); 2.9 (t, 2H); 3.6 (s, 3H); 4.06 (t, 2H); 6.92 (dd, 1H); 7.07 (d, 1H); 7.3–7.56 (m, 6H).

2-Benzyl-6-(2-diethylamino-ethoxy)-benzothiazole, Yield: 11% of theory, oil, $^1$H-NMR spectrum (200 MHz, CDCl$_3$, signals at ppm): 1.07 (t, 6H); 2.64 (q, 4H); 2.89 (t, 2H); 4.08 (t, 2H); 4.38 (s, 2H); 7.06 (dd, 1H); 7.2–7.43 (m, 6H); 7.85 (d, 1H).

2-Benzyl-6-(2-dimethylamino-ethoxy)-benzothiazole, Yield: 11% of theory, oil, $^1$H-NMR spectrum (200 MHz, DMSO-d$_6$, signals at ppm): 2.21 (s, 6H); 2.64 (t, 2H); 4.08 (t, 2H); 4.41 (s, 2H); 7.07 (dd, 1H); 7.20–7.45 (m, 5H); 7,59 (d, 1H); 7.82 (d, 1H).

2-(4-chlorobenzyl)-6-(2-diethylamino-ethoxy)-benzothiazole, Yield: 37% of theory, oil, $^1$H-NMR spectrum (200 MHz, CDCl$_3$, signals at ppm): 1.07 (t, 6H); 2.64 (q, 4H); 2.89 (t, 2H); 4.08 (t, 2H); 4.35 (s, 2H); 7.06 (dd, 1H); 7.27 (d, 1H); 7.30 (s, 4H); 7.85 (d, 1H).

2-(4-chlorobenzyl)-4-(2-diethylamino-ethoxy)-benzothiazole, Yield: 83.3% of theory, oil, $^1$H-NMR spectrum (200 MHz, DMSO-d$_6$, signals at ppm): 0.98 (t, 6H); 2.58 (q, 4H); 2.85 (t, 2H); 4.21 (t, 2H); 4.46 (s, 2H); 7.03 (d, 1H); 7.31 (m, 1H); 7.41 (s, 4H); 7.53 (d, 1H).

2-(4-chlorobenzyl)-5-(2-diethylamino-ethoxy)-benzothiazole, Yield: 49% of theory, oil, $^1$H-NMR spectrum (200 MHz, DMSO-d$_6$, signals at ppm): 1.0 (t, 6H); 2.58 (q, 4H); 2.82 (t, 2H); 4.1 (t, 2H); 4.44 (s, 2H); 7.02 (dd, 1H); 7.4 (s, 4H); 7.48 (d, 1H); 7.83 (d, 1H).

The following is obtained as a by-product:

2-(4-Chlorobenzoyl)-5-(2-diethylamino-ethoxy)-benzothiazole, Yield: 25% of theory, oil.

2-(4-chlorobenzyl)-6-[2-(morpholinyl-1)ethoxy]-benzothiazole, Yield: 37.1% of theory, oil, 1H-NMR spectrum (200 MHz, CDCl$_3$, signals at ppm): 2.59 (t, 4H); 2.82 (t, 2H); 3.73 (t, 4H); 4.15 (t, 2H); 4.36 (s, 2H); 7.07 (dd, 1H); 7.2–7.4 (m, 5H); 7.86 (d, 1H).

6-(2-Diethylamino-ethoxy)-2-(4-fluorobenzyl)-benzothiazole, Yield: 60.3% of theory, oil, $^1$H-NMR spectrum (200 MHz, DMSO-d$_6$, signals at ppm): 0.96 (t, 6H); 2.54 (q, 4H); 2.78 (t, 2H); 4.05 (t, 2H); 4.4 (s, 2H); 7.06 (dd, 1H); 7.18 (m, 2H); 7.42 (m, 2H); 7.59 (d, 1H); 7.81 (d, 1H).

The following is obtained as a by-product:

6-(2-Diethylamino-ethoxy)-2-(4-fluorobenzoyl)-benzothiazole, Yield: 6% of theory, oil.

6-(2-Diethylamino-ethoxy)-2-(2-phenylethyl)-benzothiazole, Yield: 38% of theory, oil, $^1$H-NMR spectrum (200 MHz, DMSO-d$_6$/CD$_3$OD, signals at ppm): 1.0 (t, 6H); 2.58 (q, 4H); 2.82 (t, 2H); 3.14 (t, 2H); 3.38 (t, 2H); 4.08 (t, 2H); 7.06 (dd, 1H); 7.12–7.37 (m, 5H); 7.56 (d, 1H); 7.8 (d, 1H).

2-(4-chlorobenzyl)-6-(2-diethylamino-ethoxy)-benzoxazole, Yield: 48.1% of theory, oil, $^1$H-NMR spectrum (200 MHz, DMSO-d$_6$, signals at ppm): 0.96 (t, 6H); 2.55 (q, 4H); 2.78 (t, 2H); 4.04 (t, 2H); 4.30 (s, 2H); 6.91 (dd, 1H); 7.29 (d, 1H); 7.39 (s, 4H); 7.53 (d, 1H).

6-(2-Diethylamino-ethoxy)-2-phenyl-benzothiazole, Yield: 83.4% of theory, oil, $^1$H-NMR spectrum (200 MHz, CDCl$_3$, signals at ppm): 1.09 (t, 6H); 2.66 (q, 4H); 2.92 (t, 2H); 4.12 (t, 2H); 7.1 (dd, 1H); 7.37 (d, 1H); 7.47 (m, 3H); 7.94 (d, 1H); 8.05 (m, 2H).

2-Cyclohexylmethyl-6-(2-diethylamino-ethoxy)-benzothiazole, Yield: 68.9% of theory, oil, $^1$H-NMR spectrum (200 MHz, CDCl$_3$, signals at ppm): 0.9–1.43 (t+m, 1H); 1.57–1.95 (m, 6H); 2.65 (q, 4H); 2.92 (m, 4H); 4.09 (t, 2H); 7.05 (dd, 1H); 7.3 (d, 1H); 7.84 (d, 1H).

6-(2-Diethylamino-ethoxy)-2-(2-phenylethenyl)-benzothiazole, Yield: 91.3% of theory, oil, $^1$H-NMR spectrum (200 MHz, CDCl$_3$, signals at ppm): 1.09 (t, 6H); 2.66 (q, 4H); 2.91 (t, 2H); 4.12 (t, 2H); 7.08 (dd, 1H); 7.25–7.62 (m, 8H); 7.88 (d, 1H).

2-(4-chlorobenzyl)-6-(3-diethylamino-propoxy)-benzothiazole, Yield: 36% of theory, oil, $^1$H-NMR spectrum (200 MHz, DMSO-d$_6$, signals at ppm): 0.92 (t, 6H); 1.82 (m, 2H); 2.45 (q+t, 6H); 4.04 (t, 2H); 4.42 (s, 2H); 7.07 (dd, 1H); 7.4 (s, 4H); 7.58 (d, 1H); 7.81 (d, 1H).

2-(4-chlorobenzyl)-6-(2-diisopropylamino-ethoxy)-benzothiazole, Yield: 16% of theory, oil, $^1$H-NMR spectrum (200 MHz, DMSO-d$_6$, signals at ppm): 0.98 (d, 12H); 2.78 (t, 2H); 3.02 (m, 2H); 3.92 (t, 2H); 4.41 (s, 2H); 7.05 (dd, 1H); 7.4 (s, 4H); 7.57 (d, 1H); 7.8 (d, 1H).

The following is obtained as a by-product:

2-(4-Chlorobenzoyl)-6-(2-diisopropylamino-ethoxy)-benzothiazole, Yield: 18% of theory, Melting point: 109–111° C., $^1$H-NMR spectrum (200 MHz, DMSO-d$_6$, signals at ppm): 1.0 (d, 12H); 2.84 (t, 2H); 3.03 (m, 2H); 4.03 (t, 2H); 7.24 (dd, 1H); 7.71 (d, 2H); 7.82 (d, 1H); 8.15 (d, 1H); 8.48 (d, 2H).

6-(2-Diethylamino-ethoxy)-2-(1-methylpyrrolyl-2-methyl)-benzothiazole (A) and 6-(2-Diethylamino-ethoxy)-2-(1-methylpyrrolyl-3-methyl)-benzothiazole (B), prepared from the mixture of the corresponding 6-hydroxy compounds and separation by column chromatography on neutral aluminium oxide (eluant: petroleum ether/ethyl acetate=3:1), Yield (A): 13.2% of theory, oil, $^1$H-NMR spectrum (200 MHz, DMSO-d$_6$, signals at ppm): 0.97 (t, 6H); 2.54 (q, 4H); 2.79 (t, 2H); 3.5 (s, 3H); 4.06 (t, 2H); 4.4 (s, 2H); 5.95 (m, 1H); 6.0 (m, 1H); 6.7 (m, 1H); 7.05 (dd, 1H); 7.58 (d, 1H); 7.8 (d, 1H). Yield (B): 6.5% of theory, oil, $^1$H-NMR spectrum (200 MHz, DMSO-d$_6$, signals at ppm): 0.97 (t, 6H); 2.54 (q, 4H); 2.79 (t, 2H); 3.57 (s, 3H); 4.12 (s, 2H); 5.96 (s, 1H); 6.67 (AB, 2H); 7.04 (dd, 1H); 7.55 (d, 1H); 7.77 (d, 1H).

Starting from the pure 6-hydroxy-2-(1-methylpyrrolyl-3-methyl)-benzothiazole, (B) is obtained in a yield of 87.3% of theory.

EXAMPLE 3

2-(4-Fluorobenzyl)-6-[2-(piperidinyl-1)ethoxy]-benzothiazole 266 mg (1 mmol) of 6-(2-bromoethoxy)-2-(4-fluorobenzyl)-benzothiazole and 5 ml of piperidine are refluxed for 1 hour. Then the mixture is diluted with water and extracted with methylene chloride. The extracts are dried with magnesium sulphate and after being evaporated down they are purified by column chromatography on neutral aluminium oxide (eluant: petroleum ether/ethyl acetate=2:1). Yield: 0.3 g (81% of theory), oil, $^1$H-NMR spectrum (200 MHz, DMSO-d$_6$, signals at ppm): 1.29–1.59 (m, 6H); 2.43 (bt, 4H); 2.66 (t, 2H); 4.1 (t, 2H); 4.4 (s, 2H); 7.07 (dd, 1H); 7.18 (m, 2H); 7.43 (m, 2H); 7.6 (d, 1H); 7.8 (d, 1H).

The following are prepared analogously:

6-(2-Diisoproylamino-ethoxy)-2-(4-fluorobenzyl)-benzothiazole, Yield: 77.6% of theory, oil, $^1$H-NMR spectrum (200 MHz, DMSO-d$_6$, signals at ppm): 0.98 (d, 12H); 2.78 (t, 2H); 3.01 (m, 2H); 3.92 (t, 2H); 4.4. (s, 2H); 7.04 (dd, 1H); 7.18 (m, 2H); 7.42 (m, 2H); 7.58 (d, 1H); 7.8 (d, 1H).

2-(4-Fluorobenzyl)-6-[2-(pyrrolidinyl-1)ethoxy]-benzothiazole, Yield: 54.3% of theory, Melting point: 46–48° C., $^1$H-NMR spectrum (200 MHz, DMSO-d$_6$, signals at ppm): 1.67 (m, 4H); 2.5 (m, 4H); 2.79 (t, 2H); 4.09 (t, 2H); 4.4 (s, 2H); 7.07 (dd, 1H); 7.18 (m, 2H); 7.41 (m, 2H); 7.58 (d, 1H); 7.81 (d, 1H).

2-(4-Fluorobenzyl)-6-[2-(N-(2-hydroxyethyl)-N-methylamino)-ethoxy]-benzothiazole, Yield: 77.7% of theory, oil, $^1$H-NMR spectrum (200 MHz, DMSO-d$_6$/CD$_3$OD, signals at ppm): 2.31 (s, 3H); 2.54 (t, 2H); 2.8 (t, 2H); 3.5 (t, 2H); 4.1 (t, 2H); 4.39 (s, 2H); 7.07 (dd, 1H); 7.14 (m, 2H); 7.41 (m, 2H); 7.54 (d, 1H); 7.81 (d, 1H).

6-[2-(N-Ethyl-N-(2-hydroxyethyl)amino)ethoxy]-2-(4-fluorobenzyl)-benzothiazole, Yield: 96.3% of theory, oil, $^1$H-NMR spectrum (200 MHz, DMSO-d$_6$/CD$_3$OD, signals at ppm): 0.99 (t, 3H); 2.62 (q+t, 4H); 2.87 (t, 2H); 3.48 (t, 2H); 4.06 (t, 2H); 4.4 (s, 2H); 7.01–7.24 (m, 3H); 7.35–7.5 (m, 2H); 7.56 (d, 1H); 7.81 (d, 1H).

2-(4-Fluorobenzyl)-6-[2-(4-methyl-piperazinyl-1)ethoxy]-benzothiazole, Yield: 68.5% of theory, oil, $^1$H-NMR spectrum (200 MHz, DMSO-d$_6$, signals at ppm): 2.12 (s, 3H); 2.3 (bs, 4H); 2.47 (bs, 4H); 2.69 (t, 2H); 4.1 (t, 2H); 4.4 (s, 2H); 7.06 (dd, 1H); 7.18 (m, 2H); 7.42 (m, 2H); 7.59 (d, 1H); 7.8 (d, 1H).

6-[2-(2,6-Dimethyl-piperidinyl-1)ethoxy]-2-(4-fluorobenzyl)-benzothiazole, Yield: 82.8% of theory, oil, $^1$H-NMR spectrum (200 MHz, DMSO-d$_6$, signals at ppm): 0.93–1.4 (d+m, 3H); 1.4–1.68 (m, 3H); 2.5 (m, 2H); 2.95 (t, 2H); 3.98 (t, 2H); 4.41 (s, 2H); 7.05 (dd, 1H); 7.12–7.29 (m, 2H); 7.35–7.52 (m, 2H); 7.6 (d, 1H); 7.82 (d, 1H).

2-(4-Fluorobenzyl)-6-(2-dimethylamino-ethoxy)-benzothiazole, Yield: 50.1% of theory, Melting point: 39–40° C., $^1$H-NMR spectrum (200 MHz, DMSO-d$_6$, signals at ppm): 2.22 (s, 6H); 2.64 (t, 2H); 4.09 (t, 2H); 4.4 (s, 2H); 7.06 (dd, 1H); 7.17 (m, 2H); 7.41 (m, 2H); 7.57 (d, 1H); 7.81 (d, 1H).

2-(4-chlorobenzyl)-6-[2-(N-(2-hydroxyethyl)-N-methylamino)-ethoxy]-benzothiazole, Yield: 89% of theory, Melting point: 46–48° C., $^1$H-NMR spectrum (200 MHz, DMSO-d$_6$/CD$_3$OD, signals at ppm): 2.3 (s, 3H); 2.54 (t, 2H); 2.8 (t, 2H); 3.51 (t, 2H); 4.1 (t, 2H); 4.42 (s, 2H); 7.08 (dd, 1H); 7.4 (s, 4H); 7.57 (d, 1H); 7.82 (d, 1H).

6-[2-(Bis-N,N-(2-hydroxyethyl)amino)-ethoxy]-2-(4-fluorobenzyl)-benzothiazole, Yield: 71.3% of theory, oil, $^1$H-NMR spectrum (200 MHz, DMSO-d$_6$/CD$_3$OD, signals at ppm): 2.67 (t, 4H); 2.94 (t, 2H); 3.48 (t, 4H); 4.08 (t, 2H); 4.41 (s, 2H); 7.0–7.3 (m, 3H); 7.35–7.5 (m, 2H); 7.56 (d, 1H); 7.82 (d, 1H).

2-(4-chlorobenzyl)-6-[2-(N-ethyl-N-(2-hydroxyethyl)amino)-ethoxy]-benzothiazole, Yield:-95% of theory, oil, $^1$H-NMR spectrum (200 MHz, DMSO-d$_6$/CD$_3$OD, signals at ppm): 1.0 (t, 3H); 2.6 (q+t, 4H); 2.87 (t, 2H); 3.48 (t, 2H); 4.08 (t, 2H); 4.41 (s, 2H); 7.06 (dd, 1H); 7.4 (s, 4H); 7.56 (d, 1H); 7.81 (d, 1H).

Hydrochloride (from ether): melting point: hygroscopic; Oxalate (from acetone/ether): melting point: 128–130° C.

6-[2-(Bis-N,N-(2-hydroxyethyl)amino)ethoxy]-2-(4-chlorobenzyl)-benzothiazole, Yield: 97.2% of theory, Melting point: 82–84° C., $^1$H-NMR spectrum (200 MHz, DMSO-d$_6$, signals at ppm): 2.64 (t, 4H); 2.92 (t, 2H); 3.45 (t, 4H); 4.08 (t, 2H); 4.42 (s, 2H); 7.07 (dd, 1H); 7.41 (s, 4H); 7.59 (d, 1H); 7.82 (d, 1H); Hydrochloride (from ether): melting point: 136–138° C.

2-(4-chlorobenzyl)-6-[2-(N-(2-hydroxyethyl)-N-(2-methoxyethyl)-amino)ethoxy]-benzothiazole, Yield: 71.4% of theory, oil, $^1$H-NMR spectrum (200 MHz, DMSO-d$_6$/CD$_3$OD, signals at ppm): 2.67 (t, 2H); 2.76 (t, 2H); 2.94 (t, 2H); 3.24 (s, 3H); 3.41 (t, 2H); 3.47 (t, 2H); 4.07 (t, 2H); 4.4 (s, 2H); 7.07 (dd, 1H); 7.4 (s, 4H); 7.55 (d, 1H); 7.81 (d, 1H).

6-[2-(Bis-N,N-(2-methoxyethyl)amino)ethoxy]-2-(4-chlorobenzyl)-benzothiazole, Yield: 65.4% of theory, oil, $^1$H-NMR spectrum (200 MHz, DMSO-d$_6$, signals at ppm): 2.72 (t, 4H); 2.91 (t, 2H); 3.22 (s, 6H); 3.39 (t, 4H); 4.05 (t, 2H); 4.41 (s, 2H); 7.05 (dd, 1H); 7.4 (s, 4H); 7.59 (d, 1H); 7.8 (d, 1H).

2-(4-chlorobenzyl)-6-[2-(N-ethyl-N-(2-hydroxyethyl)amino)-ethoxy]-benzoxazole, Yield: :64.1% of theory, oil, $^1$H-NMR spectrum (200 MHz, DMSO-d$_6$/CD$_3$OD, signals at ppm): 0.99 (t, 3H); 2.61 (q+t, 4H); 2.86 (t, 2H); 3.48 (t, 2H); 4.05 (t, 2H); 4.30 (s, 2H); 6.92 (dd, 1H); 7.25 (d, 1H); 7.4 (s, 4H); 7.53 (d, 1H).

2-(4-chlorobenzyl)-6-(2-diethylamino-ethoxy)-benzoxazole, Yield: 61.3% of theory, oil, $^1$H-NMR spectrum (200 MHz, DMSO-d$_6$, signals at ppm): 0.96 (t, 6H); 2.55 (q, 4H); 2.78 (t, 2H); 4.04 (t, 2H); 4.30 (s, 2H); 6.91 (dd, 1H); 7.29 (d, 1H); 7.39 (s, 4H); 7.53 (d, 1H).

2-(4-chlorobenzyl)-5-(2-diethylamino-ethoxy)-benzothiazole, Yield: 40.0% of theory, oil, $^1$H-NMR spectrum (200 MHz, DMSO-d$_6$, signals at ppm): 1.0 (t, 6H); 2.58 (q, 4H); 2.82 (t, 2H); 4.1 (t, 2H); 4.44 (s, 2H); 7.02 (dd, 1H); 7.4 (s, 4H); 7.48 (d, 1H); 7.83 (d, 1H).

2-(4-chlorobenzyl)-5-[2-(N-ethyl-N-(2-hydroxyethyl) amino)-ethoxy]-benzothiazole, Yield: 81.8% of theory, oil, $^1$H-NMR spectrum (200 MHz, DMSO-d$_6$/CD$_3$OD); signals at ppm: 1.0 (t, 3H); 2.62 (q+t, 4H); 2.88 (t, 2H); 3.49 (t, 2H); 4.1 (t, 2H); 4.44 (s, 2H); 7.02 (dd, 1H); 7.4 (s, 4H); 77.48 (d, 1H); 7.84 (d, 1H).

5-[2-(Bis-N,N-(2-hydroxyethyl)amino)ethoxy]-2-(4-chlorobenzyl)-benzothiazole, Yield: 52.9% of theory, Melting point: 49–50° C., $^1$H-NMR spectrum (200 MHz, DMSO-d$_6$/CD$_3$OD, signals at ppm): 2.69 (t, 4H); 2.96 (t, 2H); 3.49 (t, 4H); 4.1 (t, 2H); 4.44 (s, 2H); 7.03 (dd, 1H); 7.4 (s, 4H); 7.49 (d, 1H); 7.85 (d, 1H).

2-(4-chlorobenzyl)-5-[2-(piperidinyl-1)ethoxy]-benzothiazole, Yield: 49.2% of theory, Melting point: 60–63° C., $^1$H-NMR spectrum (200 MHz, DMSO-d$_6$, signals at ppm): 1.28–1.58 (bm, 6H); 2.44 (bt, 4H); 2.66 (t, 2H); 4.12 (t, 2H); 4.45 (s, 2H); 7.04 (dd, 1H); 7.42 (s, 4H); 7.5 (d, 1H); 7.87 (d, 1H).

2-(4-chlorobenzyl)-6-[2-(piperidinyl-1)ethoxy]-benzothiazole, Yield: 75.4% of theory, oil, $^1$H-NMR spectrum (200 MHz, DMSO-d$_6$, signals at ppm): 1.25–1.6 (bm, 6H); 2.42 (t, 4H); 2.65 (t, 2H); 4.1 (t, 2H); 4.41 (s, 2H); 7.07 (dd, 1H); 7.4 (s, 4H); 7.6 (d, 1H); 7.81 (d, 1H).

2-(4-chlorobenzyl)-6-[2-(N-ethyl-N-(3-hydroxypropyl) amino)-ethoxy]-benzothiazole, Yield: 93.0% of theory, oil, $^1$H-NMR spectrum (200 MHz, DMSO-d$_6$/CD$_3$OD, signals at ppm): 0.99 (t, 3H); 1.58 (m, 2H); 2.57 (q+t, 4H); 2.8 (t, 2H); 3.47 (t, 2H); 4.06 (t, 2H); 4.4 (s, 2H); 7.07 (dd, 1H); 7.4 (s, 4H); 7.56 (d, 1H); 7.82 (d, 1H).

2-(4-chlorobenzyl)-6-[2-(pyrrolidinyl-1)ethoxy]-benzothiazole, Yield: 80.7% of theory, oil, $^1$H-NMR spectrum (200 MHz, DMSO-d$_6$, signals at ppm): 1.67 (m, 4H); 2.51 (m, 4H); 2.8 (t, 2H); 4.1 (t, 2H); 4.42 (s, 2H); 7.08 (dd, 1H); 7.41 (s, 4H); 7.6 (d, 1H); 7.81 (d, 1H).

2-(4-chlorobenzyl)-6-(2-diisopropylamino-ethoxy)-benzothiazole, Yield: 42.0% of theory, oil, $^1$H-NMR spectrum (200 MHz, DMSO-d$_6$, signals at ppm): 0.98 (d, 12H); 2.78 (t, 2H); 3.02 (m, 2H); 3.92 (t, 2H); 4.41 (s, 2H); 7.05 (dd, 1H); 7.4 (s, 4H); 7.57 (d, 1H); 7.8 (d, 1H).

2-(4-chlorobenzyl)-6-[6-(N-allyl-N-methyl-amino) hexyloxy]-benzothiazole, Yield: 60% of theory, oil, $^1$H-NMR spectrum (200 MHz, DMSO-d$_6$, signals at ppm): 1.12–1.54 (bm, 6H); 1.6–1.82 (m, 2H); 2.08 (s, 3H); 2.26 (t, 2H); 2.91 (d, 2H); 3.99 (t, 2H); 5.08 (d, 1H); 5.14 (d, 1H); 5.67–5.89 (2dt, 1H); 7.06 (dd, 1H); 7.41 (s, 4H); 7.58 (d, 1H); 7.8 (d, 1H).

6-[2-(N-Methyl-N-(2-hydroxyethyl)amino)ethoxy]-2-[4-(trifluoromethyl)benzyl]-benzothiazole, Yield: 79.3% of theory, oil, $^1$H-NMR spectrum (200 MHz, DMSO-d$_6$/CD$_3$OD, signals at ppm): 2.3 (s, 3H); 2.54 (t, 2H); 2.8 (t, 2H); 3.5 (t, 2H); 4.1 (t, 2H); 4.53 (s, 2H); 7.09 (dd, 1H); 7.59 (d, 1H); 7.65 (AB, 4H); 7.82 (d, 1H).

6-[2-(N-(2-Hydroxyethyl)-N-(2-methoxyethyl)amino) ethoxy]-2-[4-(trifluoromethyl)benzyl]-benzothiazole, Yield: 90.3% of theory, oil, $^1$H-NMR spectrum (200 MHz, DMSO-d$_6$/CD$_3$OD, signals at ppm): 2.67 (t, 2H); 2.75 (t, 2H); 2.94 (t, 2H); 3.24 (s, 3H); 3.45 (2t, 4H); 4.08 (t, 2H); 4.54 (s, 2H); 7.08 (dd, 1H); 7.57 (d, 1H); 7.66 (AB, 4H); 7.82 (d, 1H).

6-(2-Dimethylamino-ethoxy)-2-[4-(trifluoromethyl) benzyl]-benzothiazole, Yield: 63.2% of theory, oil, $^1$H-NMR spectrum (200 MHz, DMSO-d$_6$, signals at ppm): 2.23 (s, 6H); 2.68 (t, 2H); 4.1 (t, 2H); 4.55 (s, 2H); 7.08 (dd, 1H); 7.64 (d, 1H); 7.67 (AD, 4H); 7.82 (d, 1H).

6-[2-(Bis-N,N-(2-hydroxyethyl)amino)ethoxy]-2-[4-(trifluoromethyl)benzyl]-benzothiazole, Yield: 65.4% of theory, oil, $^1$H-NMR spectrum (200 MHz, DMSO-d$_6$/CD$_3$OD, signals at ppm): 2.67 (t, 4H); 2.95 (t, 2H); 3.48 (t, 4H); 4.09 (t, 2H); 4.54 (s, 2H); 7.08 (dd, 1H); 7.54–7.9 (m, 6H).

6-[2-(N-Ethyl-N-(2-hydroxyethyl)amino)ethoxy]-2-[4-(trifluoromethyl)benzyl]-benzothiazole, Yield: 97.8% of theory, oil, $^1$H-NMR spectrum (200 MHz, DMSO-d$_6$/CD$_3$OD, signals at ppm): 1.0 (t, 3H); 2.61 (q+t, 2H); 2.87 (t, 2H); 3.48 (t, 2H); 4.06 (t, 2H); 4.53 (s, 2H); 7.08 (dd, 1H); 7.58 (d, 1H); 7.66 (AB, 4H); 7.82 (d, 1H).

6-[2-(Bis-N,N-(2-hydroxyethyl)amino)ethoxy]-2-(4-chlorophenylmercapto)-benzothiazole, Yield: 80% of theory, Melting point: 92–94° C., $^1$H-NMR spectrum (200 MHz, DMSO-d$_6$, signals at ppm): 2.64 (t, 4H); 2.91 (t, 2H); 3.44 (dt, 4H); 4.05 (t, 2H); 7.07 (dd, 1H); 7.55 (d, 1H); 7.61 (d, 2H); 7.76 (m, 3H).

2-(4-chlorophenylmercapto)-6-(4-diethylamino-butoxy)-benzothiazole, Yield: 64.7% of theory, oil, $^1$H-NMR spectrum (200 MHz, DMSO-d$_6$, signals at ppm): 0.92 (t, 6H); 1.4–1.82 (2m, 4H); 2.32–2.55 (q+t, 6H); 4.0 (t, 2H); 7.06 (dd, 1H);7.54 (d, 1H); 7.61 (d, 2H); 7.77 (m, 3H).

2-(4-chlorobenzylmercapto)-6-(4-diethylamino-butoxy)-benzothiazole, Yield: 88.8% of theory, oil, $^1$H-NMR spectrum (200 MHz, CDCl$_3$, signals at ppm): 1.02 (t, 6H); 1.53–1.91 (2m, 4H); 2.51 (q+t, 6H); 4.02 (t, 2H); 4.51 (s, 2H); 7.01 (dd, 1H); 7.21 (d, 1H); 7.32 (AB, 4H); 7.28 (d, 1H).

6-[2-(Bis-N,N-(2-hydroxyethyl)amino)ethoxy]-2-(4-chlorobenzylmercapto)-benzothiazole, Yield: 75.2% of theory, Melting point: 60–62° C., $^1$H-NMR spectrum (200 MHz, CDCl$_3$/CD$_3$OD, signals at ppm): 2.80 (t, 4H); 3.03 (t, 2H); 3.63 (t, 4H); 4.11 (t, 2H); 4.5 (s, 2H); 7.05 (dd, 1H); 7.24–7.45 (2m, 5H); 7.78 (d, 1H).

2-(4-Fluorophenylmercapto)-6-[2-(N-(2-hydroxyethyl)-N-methyl-amino)ethoxy]-benzothiazole, Yield: 64.4% of theory, Melting point: 48–49° C., $^1$H-NMR spectrum (200 MHz, DMSO-d$_6$/CD$_3$OD, signals at ppm): 2.28 (s, 3H); 2.5 (t, 2H); 2.78 (t, 2H); 3.5 (t, 2H); 4.08 (t, 2H); 7.05 (dd, 1H); 7.3–7.47 (m, 2H); 7.5 (d, 1H); 7.73 (d, 1H); 7.78–7.92 (m, 2H).

2-(4-chlorophenylmercapto)-6-[2-(N-ethyl-N-(2-hydroxyethyl)-amino)ethoxy]-benzothiazole, Yield: 85.6% of theory, oil, $^1$H-NMR spectrum (200 MHz, DMSO-d$_6$/CD$_3$OD, signals at ppm): 1.0 (t, 3H); 2.61 (q+t, 4H); 2.86 (t, 2H); 3.47 (t, 2H); 4.05 (t, 2H); 7.07 (dd, 1H); 7.52 (d, 1H); 7.61 (d, 1H); 7.7–7.85 (m, 3H).

6-[2-(N-Ethyl-N-(2-hydroxyethyl)amino)ethoxy]-2-(2-methyl-propyl)-benzothiazole, Yield: 71.3% of theory, oil, $^1$H-NMR spectrum (200 MHz, DMSO-d$_6$/CD$_3$OD, signals at ppm): 1.0 (t+d, 9H); 2.14 (m, 1H); 2.64 (q+t, 4H); 2.9 (t+d, 4H); 3.5 (t, 2H); 4.08 (t,2H); 7.05 (dd, 1H); 7.58 (d, 1H); 7.8 (d, 1H).

2-tert.Butyl-6-[2-(N-ethyl-N-(2-hydroxyethyl)amino)-ethoxy]-benzothiazole, Yield: 41.0% of theory, oil, $^1$H-NMR spectrum (200 MHz, DMSO-d$_6$/CD$_3$OD, signals at ppm): 1.01 (t, 3H); 1.45 (s, 9H); 2.63 (q+t, 4H); 2.88 (t, 2H); 3.49 (t, 2H); 4.09 (t, 2H); 7.06 (dd, 1H); 7.58 (d, 1H); 7.8 (d, 1H).

2-Cyclohexylmethyl-6-[2-(N-ethyl-N-(2-hydroxyethyl) amino)-ethoxy]-benzothiazole, Yield: 89.3% of theory, oil, $^1$H-NMR spectrum (200 MHz, DMSO-d$_6$/CD$_3$OD, signals at ppm): 0.85–1.4 (t+bm, 8H); 1.5–1.9 (bm, 6H); 2.61 (q, 4H); 2.9 (2t, 4H); 3.49 (t, 2H); 4.08 (t, 2H); 7.05 (dd, 1H); 7.56 (d, 1H); 7.79 (d, 1H).

6-[2-(N-Ethyl-N-(2-hydroxyethyl)amino)ethoxy]-2-(n-pentyl)-benzothiazole, Yield: 85.4% of theory, oil, $^1$H-NMR spectrum (200 MHz, DMSO-d$_6$/CD$_3$OD, signals at ppm): 0.9 (bt, 3H); 1.0 (t, 3H); 1.37 (bm, 4H); 1.8 (bm, 2H); 2.61 (q+t, 4H); 2.89 (t, 2H); 3.04 (t, 2H); 3.49 (t, 2H); 4.08 (t, 2H); 7.05 (dd, 1H); 7.56 (d, 1H); 7.79 (d, 1H).

6-(2-Diethylamino-ethoxy)-2-(naphthyl-2-methyl)-benzothiazole, Yield: 52.0% of theory, oil, $^1$H-NMR spectrum (200 MHz, DMSO-d$_6$, signals at ppm): 0.95 (t, 6H); 2.54 (q, 4H); 2.78 (t, 2H); 4.05 (t, 2H); 4.59 (s, 2H); 7.06 (dd, 1H); 7.44–7.62 (m, 4H); 7.78–8.0 (m, 5H).

6-[2-(N-Ethyl-N-(2-hydroxyethyl)amino)ethoxy]-2-(naphthyl-1-methyl)-benzothiazole, Yield: 75.6% of theory, Melting point: 51–53° C., $^1$H-NMR spectrum (200 MHz, DMSO-d$_6$/CD$_3$OD, signals at ppm): 0.97 (t, 3H); 2.6 (q+t, 4H); 2.84 (t, 2H); 3.46 (t, 2H); 4.04 (t, 2H); 4.9 (s, 2H); 7.04 (dd, 1H); 7.44–7.7 (m, 5H); 7.81 (d, 1H); 7.87–8.2 (2m, 3H).

6-(2-Diethylamino-ethoxy)-2-(naphthyl-1-methyl)-benzothiazole, Yield: 84.7% of theory, Melting point: 48–50° C., $^1$H-NMR spectrum (200 MHz, DMSO-d$_6$, signals at ppm): 0.95 (t, 6H); 2.52 (q, 4H); 2.75 (t, 2H); 4.01 (t, 2H); 4.89 (s, 2H); 7.04 (dd, 1H); 7.45–7.68 (m, 5H); 7.81 (d, 1H); 7.86–8.18 (2m, 3H).

6-[2-(N-Ethyl)-N-(2-hydroxyethyl)amino)ethoxy]-2-(naphthyl-2-methyl)-benzothiazole, Yield: 64.2% of theory, oil, $^1$H-NMR spectrum (200 MHz, DMSO-d$_6$/CD$_3$OD, signals at ppm): 0.98 (t, 3H); 2.6 (q+t, 4H); 2.86 (t, 2H); 3.47 (t, 2H); 4.07 (t, 2H); 4.59 (s, 2H); 7.07 (dd, 1H); 7.44–7.60 (m, 4H); 7.76–7.98 (m, 5H).

6-[2-(Piperidinyl-1)ethoxy]-2-(thienyl-2-methyl)-benzothiazole, Yield: 59.7% of theory, oil, $^1$H-NMR spectrum (200 MHz, DMSO-d$_6$, signals at ppm): 1.3–1.58 (bm, 6H); 2.44 (bt, 4H); 2.67 (t, 2H); 4.1 (t, 2H); 4.64 (s, 2H); 6.98–7.14 (m, 3H); 7.45 (dd, 1H); 7.62 (d, 1H); 7.83 (d, 1H).

6-(2-Diethylamino-ethoxy)-2-(thienyl-2-methyl)-benzothiazole, Yield: 66.4% of theory, oil, $^1$H-NMR spectrum (200 MHz, DMSO-d$_6$, signals at ppm): 0.97 (t, 6H); 2.55 (q, 4H); 2.79 (t, 2H); 4.06 (t, 2H); 4.62 (s, 2H); 6.96–7.13 (m, 3H); 7.42 (dd, 1H); 7.58 (d, 1H); 7.81 (d, 1H).

6-[2-(N-Ethyl-N-(2-hydroxyethyl)amino)ethoxy]-2-(pyridyl-2-methyl)-benzothiazole, Yield: 26.6% of theory, oil, $^1$H-NMR spectrum (200 MHz, DMSO-d$_6$/CD$_3$OD, signals at ppm): 1.0 (t, 3H); 2.6 (q+t, 4H); 2.87 (t, 2H); 3.48 (t, 2H); 4.08 (t, 2H); 4.56 (s, 2H); 7.07 (dd, 1H); 7.3 (m, 1H); 7.47 (d, 1H); 7.57 (d, 1H); 7.77 (dd, 1H); 7.81 (d, 1H); 8.55 (d, 1H).

6-[2-(N-Ethyl-N-(2-hydroxyethyl)amino)ethoxy]-2-(pyridyl-4-methyl)-benzothiazole, Yield: 25% of theory, oil, $^1$H-NMR spectrum (200 MHz, DMSO-d$_6$/CD$_3$OD, signals at ppm): 1.0 (t, 3H); 2.61 (q+t, 4H); 2.88 (t, 2H); 3.48 (t, 2H); 4.1 (t, 2H); 4.45 (s, 2H); 7.08 (dd, 1H); 7.39 (d, 2H); 7.56 (d, 1H); 7.82 (d, 1H); 8.53 (d, 2H).

2-(4-chlorobenzyl)-6-(4-diethylamino-butoxy)-benzothiazole-hydrochloride, from 6-(4-bromo-butoxy)-2-(4-chlorobenzyl)-benzothiazole and diethylamine and subsequent formation of the hydrochloride using ethereal hydrochloric acid. Yield: 25.0% of theory, Melting point: 202–204° C., $^1$H-NMR spectrum (200 MHz, DMSO-d$_6$/CD$_3$OD, signals at ppm): 1.22 (t, 6H); 1.83 (bt, 4H); 3.14 (q+t, 6H); 4.08 (bt, 2H); 4.42 (s, 2H); 7.09 (dd, 1H); 7.41 (s, 4H); 7.58 (d, 2H); 4.42 (s, 2H); 7.09 (dd, 1H); 7.41 (s, 4H); 7.58 (d, 1H); 7.84 (d, 1H).

6-[2-(N-Allyl-N-methyl-amino)ethoxy]-2-[4-(trifluoromethyl)benzyl]-benzothiazole, Yield: 61% of theory, oil, Melting point: 202–204° C., $^1$H-NMR spectrum (200 MHz, DMSO-d$_6$, signals at ppm): 2.23 (s, 3H); 2.73 (t, 2H); 3.06 (d, 2H); 4.11 (t, 2H); 4.55 (s, 2H); 5.12 (d, 1H); 5.19 (d, 1H); 5.72–5.94 (2dt, 1H); 7.07 (dd, 1H); 7.62 (d, 1H); 7.68 (AB, 4H); 7.82 (d, 1H).

2-(4-chlorobenzyl)-6-[6-(N-(2-hydroxyethyl)-N-methyl-amino)hexyloxy]-benzothiazole, Yield: 91% of theory, oil Melting point: waxy, $^1$H-NMR spectrum (200 MHz, DMSO-d$_6$/CD$_3$OD, signals at ppm): 1.22–1.55 (bm, 6H); 1.65–1.85 (bm, 2H); 2.17 (s, 3H); 2.25–2.46 (2t, 4H); 3.47 (t, 2H); 4.0 (t, 2H); 4.42 (s, 2H); 7.07 (dd, 1H); 7.4 (s, 4H); 7.55 (d, 1H); 7.81 (d, 1H).

EXAMPLE 4

2-(4-chlorobenzyl)-6-[2-(N-(2-acetoxyethyl)-N-ethylamino)-ethoxy]-benzothiazole 0.39 g (1 mmol) of 2-(4-chlorobenzyl)-6-[2-(N-ethyl-N-(2-hydroxyethyl)amino)ethoxy]-benzothiazole are dissolved in 25 ml of methylene chloride and after the addition of 0.20 g (2 mmol) of triethylamine and 0.12 g (1.5 mmol) of acetyl chloride the mixture is stirred for 2 hours at ambient temperature. Then aqueous sodium hydrogen carbonate solution was added, the resulting mixture was stirred for 10 minutes and then the organic phase was separated off. It was dried over magnesium sulphate and evaporated down. Yield: 93% of theory, oil $^1$H-NMR spectrum (200 MHz, DMSO-d$_6$, signals at ppm): 0.98 (t, 3H); 1.97 (s, 3H); 2.61 (q, 2H); 2.74 (t, 2H); 2.87 (t, 2H); 4.06 (2t, 4H); 4.42 (s, 2H); 7.05 (dd, 1H); 7.41 (s, 4H); 7.6 (d, 1H); 7.81 (d, 1H).

The following are prepared analogously:

2-(4-chlorobenzyl)-6-[2-(N-ethyl-N-(2-pivaloyloxyethyl)-amino)-ethoxy]-benzothiazole, Yield: 95% of theory, oil, $^1$H-NMR spectrum (200 MHz, DMSO-d$_6$, signals at ppm): 0.99 (t, 3H); 1.1 (s, 9H); 2.61 (q, 2H); 2.75 (t, 2H); 2.88 (t, 2H); 4.08 (2t, 4H); 4.42 (s, 2H); 7.06 (dd, 1H); 7.4 (s, 4H); 7.59 (d, 1H); 7.81 (d, 1H). Hydrochloride (from ether): Melting point: from 70° C.

2-(4-chlorophenylmercapto)-6-[2-(N-ethyl-N-(2-pivaloyloxyethyl)amino)ethoxy]-benzothiazole, Yield: 83.7% of theory, oil, $^1$H-NMR spectrum (200 MHz, DMSO-$d_6$, signals at ppm): 0.97 (t, 3H); 1.1 (s, 9H); 2.61 (q, 2H); 2.74 (t, 2H); 2.87 (t, 2H); 4.07 (2t, 4H); 7.07 (dd, 1H); 7.5–7.85 (2m, 6H).

2-(4-chlorobenzyl)-6-[2-(N-ethyl-N-(2-pivaloyloxyethyl)-amino)-ethoxy]-benzoxazole, Yield: 84.8% of theory, oil, $^1$H-NMR spectrum (200 MHz, DMSO-$d_6$, signals at ppm): 0.98 (t, 3H); 1.1 (s, 9H); 2.6 (q, 2H); 2.75 (t, 2H); 2.86 (t, 2H); 4.06 (2t, 4H); 4.3 (s, 2H); 6.9 (dd, 1H); 7.28 (d, 1H); 7.4 (s, 4H); 7.54 (d, 1H).

6-[2-(N-Ethyl-N-(2-pivaloyloxyethyl)amino)ethoxy]-2-[4-(trifluoromethyl)benzyl]-benzothiazole, Yield: 90.4% of theory, oil, $^1$H-NMR spectrum (200 MHz, DMSO-$d_6$, signals at ppm): 0.98 (t, 3H); 1.1 (s, 9H); 2.61 (q, 2H); 2.75 (t, 2H); 2.88 (t, 2H); 4.07 (m, 4H); 4.54 (s, 2H); 7.06 (dd, 1H); 7.59 (d, 1H); 7.68 (AB, 4H); 7.83 (d, 1H).

6-[2-(N-Ethyl-N-(2-pivaloyloxyethyl)amino)ethoxy]-2-(4-fluorobenzyl)-benzothiazole, Yield: 91.8% of theory, oil, $^1$H-NMR spectrum (200 MHz, DMSO-$d_6$, signals at ppm): 0.98 (t, 3H); 1.1 (s, 9H); 2.61 (q, 2H); 2.75 (t, 2H); 2.88 (t, 2H); 4.1 (m, 4H); 4.42 (s, 2H); 7.07 (dd, 1H); 7.12–7.27 (m, 2H); 7.38–7.5 (m, 2H); 7.6 (d, 1H); 7.82 (d, 1H).

EXAMPLE 5

2-(4-chlorobenzylmercapto)-6-[2-(N-(n-hexyl)-N-methyl-amino)-ethoxy]-benzothiazole a) 2-(4-chlorobenzylmercapto)-6-(2-methylamino-ethoxy)-benzothiazole Prepared from 6-(2-bromoethoxy)-2-(4-chlorobenzyl-mercapto)-benzothiazole and methylamine analogously to Example 3. Yield: 97.5% of theory, Melting point: 56–58° C., $^1$H-NMR spectrum (200 MHz, CDCl$_3$, signals at ppm): 1.56 (s, 1H); 2.52 (s, 3H); 3.0 (t, 2H); 4.22 (t, 2H); 4.51 (s, 2H); 7.03 (dd, 1H); 7.23 (d, 1H); 7.33 (AB, 4H); 7.77 (d, 1H).

b) 2-(4-Chlorobenzylmercapto)-6-[2-(N-(n-hexyl)-N-methyl-amino)-ethoxy]-benzothiazole 0.7 g (1.92 mMol) of 2-(4-chlorobenzylmercapto)-6-(2-N-methylamino-ethoxy)-benzothiazole are dissolved in 20 ml of dimethylformamide and after the addition of 0.5 g (3 mMol) of 1-bromohexane and 1.38 g (10 mMol) of potassium carbonate the mixture is stirred for 24 hours at ambient temperature. Then it is evaporated down in vacuo, taken up in water and extracted with ethyl acetate. The residue remaining after evaporation of the extracts is purified by column chromatography on neutral aluminium oxide (eluant: petroleum ether/ethyl acetate=5:1). Yield: 24.3% of theory, oil, $^1$H-NMR spectrum (200 MHz, CDCl$_3$, signals at ppm): 0.9 (m, 3H); 1.13–1.65 (2m, 8H); 23.5 (s, 3H); 2.45 (t, 2H); 2.81 (t, 2H); 4.1 (t, 2H); 4.51 (s, 2H); 7.03 (dd, 1H); 7.22 (d, 1H); 7.32 (AB, 4H); 7.77 (d, 1H).

EXAMPLE 6

Tablets containing 5 mg of active substance

| Composition: 1 tablet contains: | |
|---|---|
| active substance | 5.0 mg |
| lactose | 148.0 mg |
| potato starch | 65.0 mg |
| magnesium stearate | 2.0 mg |
| | 220.0 mg |

Method of Preparation

A 10% mucilage is prepared from potato starch by heating. The active substance, lactose and remaining potato starch are mixed and granulated with the above mucilage through a 1.5 mm mesh sieve. The granules are dried at 45° C., passed through the same sieve again, mixed with magnesium stearate and compressed to form tablets.

Weight of tablet: 220 mg

Die: 9 mm

EXAMPLE 7

Coated tablets containing 5 mg of active substance

The tablets prepared in Example I are coated by known methods with a coating consisting essentially of sugar and talc. The finished coated tablets are polished with beeswax.

Weight of coated tablet: 300 mg

EXAMPLE 8

Suppositories containing 5 mg of active substance

| Composition: 1 suppository contains: | |
|---|---|
| active substance | 5.0 mg |
| suppository mass (e.g. Witepsol W 45 ®) | 1 695.0 mg |
| | 1 700.0 mg |

Method of Preparation

The finely powdered active substance is suspended in the molten suppository mass and cooled to 40° C. The mass at 37° C. is poured into slightly chilled suppository moulds. Weight of suppository: 1.7 g.

EXAMPLE 9

Capsules containing 5 mg of active substance

| Composition: 1 capsule contains | |
|---|---|
| active substance | 5.0 mg |
| lactose | 82.0 mg |
| starch | 82.0 mg |
| magnesium stearate | 1.0 mg |
| | 170.0 mg |

Method of Preparation

The powder mixture is thoroughly mixed and packed into size 3 hard gelatin capsules in a capsule filling machine, whilst continuously monitoring the final weight.

EXAMPLE 10

Cream for topical application containing 1 g of active substance

A formulation for topical application of the compounds of formula I may have the following composition

| | | |
|---|---|---|
| 1. active substance | 1.0 g | |
| 2. stearyl alcohol | 4.0 g | |
| 3. cetyl alcohol | 4.0 g | |
| 4. mineral oil | 3.0 g | |
| 5. Polysorbate 60 | 4.5 g | |
| 6. sorbitan stearate | 4.5 g | |
| 7. propylene glycol | 10.0 g | |
| 8. methylparaben | 0.18 g | |
| 9. propylparaben | 0.02 g | |
| 10. water | q.s. ad 100.00 g | |

Ingredients 2–6 are heated to 80° C. until everything has melted; Then ingredient 1 is dissolved in the oily phase. Ingredients 7 and 10 are heated to 90° C. and ingredients 8 and 9 are dissolved in the aqueous phase thus obtained. Then the aqueous phase is added to the oil phase and stirred quickly to form an emulsion. The emulsion is then left to cool slowly to 50° C. in order to solidify. Whilst stirring is continued the preparation is cooled to ambient temperature.

EXAMPLE 11

Feed for laying hens

| Composition: | |
|---|---|
| maize | 633 g/kg |
| soya bean meal | 260 g/kg |
| meat meal | 40 g/kg |
| edible fat | 25 g/kg |
| soya oil | 17 g/kg |
| bicalcium phosphate | 12 g/kg |
| calcium carbonate | 6 g/kg |
| Vitamin/mineral mixture | 5 g/kg |
| active substance | 2 g/kg |

These components, carefully mixed in the quantities specified, yield 1 kg of feed.

We claim:

1. A compound of the formula I

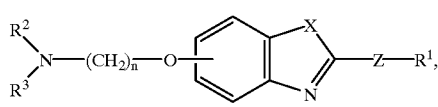

(I)

or a pharmaceutically acceptable acid addition salt thereof, wherein, n denotes the number 2, 3, 4, 5 or 6, X is a sulphur atom, Z is a bond, an oxygen or sulphur atom or a sulphonyl group, $R^1$ denotes a straight-chained or branched $C_{1-8}$-alkyl group or a straight-chained $C_{2-6}$-alkenyl group, which may optionally be substituted by 1 to 3 methyl groups, whilst both the alkyl group and the alkenyl group may be terminally substituted by a $C_{3-7}$-cycloalkyl group, by a phenyl or naphthyl group, by a 5-membered heteroaryl group bound via a carbon atom which contains an optionally alkyl-substituted imino group, an oxygen or sulphur atom or a nitrogen atom and an oxygen or sulphur atom or an optionally alkyl-substituted imino group, whilst the above-mentioned phenyl groups may each be mono- or disubstituted by a halogen atom, an alkyl, trifluoromethyl, cyano or nitro group, and $R^2$ and $R^3$, which may be identical or different, each denote a straight-chained or branched $C_{1-6}$-alkyl group which may be terminally substituted by a hydroxy, alkyloxy or alkylcarbonyloxy group, wherein the alkyl moieties may in each case be straight-chained or branched and may comprise 1 to 6 carbon atoms, or a straight-chained or branched $C_{3-6}$-alkenyl group, or $R^2$ and $R^3$ together with the nitrogen atom between them denote a 5-membered saturated monocyclic ring, which may additionally be substituted in the carbon skeleton by one or two alkyl groups, whilst each of the aforementioned halogen atoms is selected from fluorine, chlorine, bromine or iodine atom and, unless otherwise specified, each of the aforementioned alkyl groups contains 1 to 3 carbon atoms.

2. A compound of the formula I according to claim 1, or a pharmaceutically acceptable acid addition salt thereof, wherein, each 5-membered heteroaryl group is selected from 2-thienyl, 3-thienyl, 2-furyl, 3-furyl, 1H-pyrrol-2-yl, 1H-pyrrol-3-yl, 1-methylpyrrol-2-yl, 1-methylpyrrol-3-yl, 2-imidazolyl, 4-imidazolyl, 1,3-oxazol-2-yl, 1,3-oxazol-4-yl, 1,3-oxazol-5-yl, 3-pyrazolyl, 4-pyrazolyl, 3-isoxazolyl, 4-isoxazolyl or 5-isoxazolyl.

3. A compound of the formula Ia

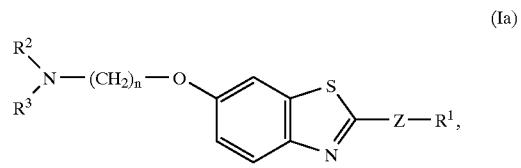

(Ia)

or a pharmaceutically acceptable salt thereof, wherein, n denotes the number 2, 3, 4, 5 or 6, Z is a bond, an oxygen or sulphur atom or a sulphonyl group, $R^1$ denotes a a straight-chained or branched $C_{1-8}$-alkyl group or a straight-chained $C_{2-6}$-alkenyl group, which may optionally be substituted by 1 to 3 methyl groups, whilst both the alkyl group and the alkenyl group may be terminally substituted by a $C_{3-7}$-cycloalkyl group, by a phenyl or naphthyl group, by a 5-membered heteroaryl group bound via a carbon atom which contains an optionally alkyl-substituted imino group, an oxygen or sulphur atom or a nitrogen atom and an oxygen or sulphur atom or an optionally alkyl-substituted imino group, whilst the above-mentioned phenyl groups may each be mono- or disubstituted by a halogen atom, an alkyL, trifluoromethyl, cyano or nitro group, and $R^2$ and $R^3$, which may be identical or different, each denote a straight-chained or branched $C_{1-6}$-alkyl group which may be terminally substituted by a hydroxy, alkyloxy or alkylcarbonyloxy group, wherein the alkyl moieties may in each case be straight-chained or branched and may comprise 1 to 6 carbon atoms, or a straight-chained or branched $C_{3-6}$-alkenyl group, or $R^2$ and $R^3$ together with the nitrogen atom between them denote a 5-, 6- or 7-membered saturated monocyclic ring, which may additionally be substituted in the carbon skeleton by one or two alkyl groups, whilst each of the aforementioned halogen atoms is selected from fluorine, chlorine, bromine and iodine, whilst each of the aforementioned alkyl groups, unless otherwise specified, contains 1 to 3 carbon atoms, and whilst each of the aforementioned 5-membered heteroaryl groups is selected from 2-thienyl, 3-thienyl, 2-furyl, 3-furyl, 1H-pyrrol-2-yl, 1H-pyrrol-3-yl, 1-methylpyrrol-2-yl, 1methylpyrrol-3-yl, 2-imidazolyl, 4-imidazolyl, 1,3-oxazol-2-yl, 1,3-oxazol-4-yl, 1,3-oxazol-5-yl, 3-pyrazolyl, 4-pyrazolyl, 3-isoxazolyl, 4-isoxazolyl or 5-isoxazolyl.

4. A compound of the formula Ia according to claim 3, or a pharmaceutically acceptable salt thereof, wherein, n denotes the number 2, 3, 4, 5 or 6, Z denotes a bond, an oxygen or sulphur atom, $R^1$ denotes a straight-chained $C_{1-5}$-alkyl group optionally substituted by 1 to 3 methyl groups, whilst a straight-chained $C_{1-3}$-alkyl group may additionally be terminally substituted by a $C_{5\ or\ 6}$-cycloalkyl ring, by a phenyl, 1-naphthyl, 2-naphthyl, 2-thienyl, 1H-pyrrol-2-yl, 1H-pyrrol-3-yl, 1-methylpyrrol-2-yl or 1-methylpyrrol-3-yl group, or a 2-phenylethenyl group, whilst the above-mentioned phenyl groups may each be monosubstituted by a fluorine or chlorine atom or by a methyl, trifluoromethyl, cyano or nitro group or may be disubstituted by a methyl and a nitro group, and $R^2$ and $R^3$, which may be identical or different, each denote a straight-chained or branched $C_{1-3}$-alkyl group which may be terminally substituted by a hydroxy, alkyloxy or alkylcarbonyloxy group, whilst the alkyl moieties in each case may be straight-chained or branched and may contain 1 to 4 carbon atoms, or an allyl group, or $R^2$ and $R^3$ together with the nitrogen atom between them denote a 1-pyrrolidinyl ring.

5. A compound of the formula Ia according to claim 3, or a pharmaceutically acceptable salt thereof, wherein, n denotes the number 2, Z is a bond, and $R^1$ is a methyl group which is substituted by a phenyl group optionally substituted in the 4-position by a fluorine or chlorine atom or a methyl or trifluoromethyl group, or is substituted by a 1-methylpyrrol-3-yl group, or Z denotes a sulphur atom, $R^1$ denotes a 2,2-dimethyl-propyl, 4-chlorobenzyl or 4-fluorobenzyl group, and $R^2$ and $R^3$, which may be identical or different, denotes a methyl, ethyl or 2-hydroxyethyl group.

6. A compound selected from the class consisting of:

(a) 6-(2-Dimethylamino-ethoxy)-2-(4-fluorobenzyl)-benzothiazole,
(b) 6-(2-Diethylamino-ethoxy)-2-(4-fluorobenzyl)-benzothiazole,
(c) 6-[2-(N-(2-Hydroxyethyl)-N-methyl-amino)ethoxy]-2-[4-(trifluoromethyl)benzyl]-benzothiazole,
(d) 6-(2-Diethylamino-ethoxy)-2-(1-methylpyrrolyl-3-methyl)-benzothiazole,
(e) 6-[2-(N.N-Bis-(2-hydroxyethyl)amino)ethoxy]-2-(4-fluorobenzyl)-benzothiazole,
(f) 6-[2-(N.N-Bis-(2-hydroxyethyl)amino)ethoxy]-2-(4-chlorophenylmercapto)-benzothiazole,
(g) 2-(4-Chlorobenzyl)-6-[2-(N-ethyl-N-(2-hydroxyethyl)amino)-ethoxy]-benzothiazole,
(h) 6-[N.N-Bis-(2-hydroxyethyl)amino)ethoxy]-2-(4-chlorobenzyl)-benzothiazole,
(i) 6-[2-(N.N-Bis-(2-hydroxyethyl)amino)ethoxy]-2-[4-(trifluoromethyl)benzyl]-benzothiazole,
(j) 2-(4-Chlorobenzyl)-6-[2-(N-(2-hydroxyethyl)-N-methyl-amino)ethoxy]-benzothiazole,
(k) 2-(4-Chlorobenzyl)-6-(2-diethylamino-ethoxy)-benzothiazole,
(l) 2-(4-Chlorobenzylmercapto)-6-(2-diethylamino-ethoxy)-benzothiazole,
(m) 6-(2-Diethylamino-ethoxy)-2-(2,2-dimethyl-propylmercapto)-benzothiazole, of gallstones, a therapeutic amount of a compound in accordance with claim 1, 2, 3, 4, 5 or 6.

7. A pharmaceutical composition comprising a compound according to claim 1, 2, 3, 4, 5 or 6, and a pharmaceutically acceptable carrier or diluent.

8. A method for inhibiting cholesterol biosynthesis which comprises administering, to an animal suffering from the excessive biosynthesis of cholesterol, a cholesterol biosynthetic inhibiting amount of a compound in accordance with claim 1, 2, 3, 4, 5 or 6.

9. A method for treating hypercholesterolaemia which comprises administering, to an animal suffering from hypercholesterolaemia, a cholesterol biosynthesis inhibiting amount of a compound in accordance with claim 1, 2, 3, 4, 5 or 6.

10. A method for treating a disease condition characterized by excessive cell proliferation which comprises administering, to an animal suffering from such condition, an antiproliferative amount of a compound in accordance with claim 1, 2, 3, 4, 5 or 6.

11. A method for preventing or treating gallstones which comprises administering, to an animal suffering from a gallstone or susceptible to the formation $R^2$ and $R^3$, which may be identical or different, denotes a methyl, ethyl or 2-hydroxyethyl group.

12. A method for treating a mycosal infection which comprises administering, to an animal suffering from a mycosal infection, a therapeutic amount of a compound in accordance with claim 1, 2, 3, 4, 5 or 6.

13. Feed for laying hens, comprising a compound in accordance with claim 1, 2, 3, 4, 5 or 6.

14. A method for causing hens to lay eggs having reduced cholesterol content, which method comprises administering to said hens an amount of a compound in accordance with claim 1, 2, 3, 4, 5 or 6 which is sufficient to cause a reduction in the cholesterol content of eggs laid by said hens.

* * * * *